(12) United States Patent
Farberov

(10) Patent No.: US 7,125,119 B2
(45) Date of Patent: Oct. 24, 2006

(54) UNIVERSAL GONIOSCOPE-CONTACT LENS SYSTEM FOR OBSERVATION AND INTRAOCULAR LASER SURGERY

(76) Inventor: Arkadiy Farberov, 42257 Troyer Ave., Fremont, CA (US) 94539

( * ) Notice: Subject to any disclaimer, the term of this patent is extended or adjusted under 35 U.S.C. 154(b) by 0 days.

(21) Appl. No.: 11/263,213

(22) Filed: Nov. 1, 2005

(65) Prior Publication Data

US 2006/0050229 A1   Mar. 9, 2006

Related U.S. Application Data

(63) Continuation-in-part of application No. 10/409,428, filed on Apr. 7, 2003, now Pat. No. 6,942,343.

(51) Int. Cl.
*A61B 3/10* (2006.01)
*A61B 3/117* (2006.01)

(52) U.S. Cl. .................. 351/219; 351/205; 606/4; 606/5; 606/10

(58) Field of Classification Search ............. 351/200, 351/205, 219, 246
See application file for complete search history.

(56) References Cited

U.S. PATENT DOCUMENTS

| | | | |
|---|---|---|---|
| 4,728,183 A | 3/1988 | Heacock et al. | |
| 5,046,836 A | 9/1991 | Volk | |
| 5,252,998 A | 10/1993 | Reis et al. | |
| 5,309,187 A | 5/1994 | Crossman et al. | |
| 5,347,326 A | 9/1994 | Volk | |
| 5,359,372 A * | 10/1994 | Kida et al. | 351/219 |
| 5,479,222 A * | 12/1995 | Volk | 351/219 |
| 5,523,810 A | 6/1996 | Volk | |
| 5,548,352 A | 8/1996 | Dewey | |
| 5,549,596 A * | 8/1996 | Latina | 606/4 |
| 5,805,269 A | 9/1998 | Volk | |
| 5,841,510 A | 11/1998 | Roggy | |
| 5,953,097 A * | 9/1999 | Stark | 351/219 |
| 6,019,472 A * | 2/2000 | Koester et al. | 351/219 |
| 6,698,886 B1 * | 3/2004 | Pollack et al. | 351/219 |
| 6,767,098 B1 | 7/2004 | Erickson et al. | |
| 6,942,343 B1 | 9/2005 | Farberov | |
| 2002/0167644 A1 | 11/2002 | Pollack | |

FOREIGN PATENT DOCUMENTS

RU         2125426        1/1999

* cited by examiner

*Primary Examiner*—Charles A. Marmor, II
*Assistant Examiner*—John R Sanders

(57) ABSTRACT

The invention provides a universal gonioscope-contact lens system suitable for diagnostics and intraocular laser surgery. The device consists of a hollow gonioscope body with a plurality of mirrors on the inner walls of the body and a contact lens. The front part of the lens is intended for contact with the eye cornea, while the rear part of the lens has a tapered shape with flat portions arranged perpendicular to the beams reflected from the gonioscope mirrors. The tapered portion of the lens can be conveniently used for manipulating the lens and for arranging optical lens components such as a concave lens and convex lens.

23 Claims, 15 Drawing Sheets (A)

(B)

(C)

UNIVERSAL GONIOSCOPE-CONTACT LENS SYSTEM FOR OBSERVATION AND INTRAOCULAR LASER SURGERY

CROSS-REFERENCES TO RELATED APPLICATIONS

The present patent application is a continuation-in-part application related to U.S. patent application Ser. No. 10/409,428 filed on Apr. 7, 2003 by Arkadiy Farberov (now U.S. Pat. No. 6,942,343 issued on Sep. 13, 2005) and entitled "Optical Device for Intraocular Observation).

FIELD OF THE INVENTION

The present invention relates to optical devices for indirect ophthalmology, in particular to gonioscopes for intraocular observation and laser surgery. More specifically, the invention relates to a universal gonioscope—contact lens system suitable for both observation and/or intraocular laser surgery.

FIELD OF THE INVENTION

For better understanding the principle of the present invention and for understanding the areas of application of the invented device, it would be advantageous to briefly familiars yourself with anatomy of the eye. FIG. 1 is a cross-sectional view of a human eye. The definitions of the terms some of which are used in the description of the present patent application are given below.

The anterior chamber is the area bounded in front by the cornea and in back by the lens, and filled with aqueous.

The choroid, which carries blood vessels, is the inner coat between the sclera and the retina.

The ciliary body is an unseen part of the iris, and these together with the ora serrata form the uveal tract.

The conjunctiva is a clear membrane covering the white of the eye (sclera).

The cornea is a clear, transparent portion of the outer coat of the eyeball through which light passes to the lens.

Fundus is an inner wall of the eye.

The iris gives our eyes color and it functions like the aperture on a camera, enlarging in dim light and contracting in bright light. The aperture itself is known as the pupil.

The macula is a small area in the retina that provides our most central, acute vision.

The optic nerve conducts visual impulses to the brain from the retina.

The ora serrata and the ciliary body form the uveal tract, an unseen part of the iris.

The posterior chamber is the area behind the iris, but in front of the lens, that is filled with aqueous.

The pupil is the opening, or aperture, of the iris.

Retina is the innermost coat of the back of the eye, formed of light-sensitive nerve endings that carry the visual impulse to the optic nerve. The retina may be compared to the film of a camera.

The sclera is the white of the eye.

The vitreous is a transparent, colorless mass of soft, gelatinous material filling the eyeball behind the lens.

Glaucoma is a group of eye diseases causing optic nerve damage.

Elevated intraocular pressure is frequently an early sign of the disease. Reduction of the intraocular pressure may prevent loss of vision. The goniolaser lens may be designed to focus the laser light to treat two specific types of glaucoma.

Angle-closure glaucoma: In angle-closure glaucoma the intraocular fluids (aqueous humor) must pass through the pupil from behind the iris (posterior chamber) to a position in from of the iris (anterior chamber). The aqueous humor then escapes from the eye through microscopic channels located at the angle of the anterior chamber between the peripheral iris and cornea. In angle-closure glaucoma there occurs a block at the pupil so that the aqueous humor cannot pass from the posterior to the anterior chamber and the eye pressure becomes very elevated.

Open-angle glaucoma: Open-angle glaucoma is caused by an abnormality in the microscopic channels, trabecular meshwork, that are located in the angle of the anterior chamber. Eyedrop medications may help the aqueous humor to pass through the meshwork, but not in all cases.

The techniques used for viewing the inner parts of the eye, such as retina and anterior chamber angle of the eye, for evaluation, management, and classification of normal and abnormal structures is known as gonioscopy, and devices used for gonioscopy are known as gonioscopes. Observation of the anterior chamber and especially its angle areas, which are difficult or impossible to see with the use of some conventional optical means, is very important for diagnosis of eye diseases. For example, the classification of glaucoma relies heavily upon knowledge of the anterior segment anatomy, particularly that of the anterior chamber angle.

The anterior chamber of a human eye is commonly evaluated during slit lamp biomicroscopy, but the chamber angle is hidden from ordinary view because of total internal reflection of light rays emanating from the angle structures. In other words, without gonioscopy, the additional diagnostic clues of disease are forever hidden from ordinary view. It requires additional effort, skill, and patient cooperation to view the normally concealed chamber angle by either indirect (angle structures viewed through a mirror) or direct (angle structures viewed directly) gonioscopic techniques. In other words, without gonioscopy, it is impossible to classify the glaucoma properly.

Heretofore, many gonioscopic devices have been known. The basic gonioscopic instrument used in the art is known as a Goldman "universal" lens and mirrors or Roussel lens assembly. This gonioscope comprises an optical body with flat tapered sides having an entrance face which is flat or spherical, a spherical exit face which is applied to the cornea of the eye, a reflecting face and a compensating element, for example a piano-cylindrical lens. The Goldman gonioscope is a universal three-reflection lens assembly for biomicroscopic investigation and laser coagulation of the eye bottom and the front camera angle of the eye. With the help of lenses by Goldman in combination with a binocular microscope of a slit lamp a high quality image, a step-by-step observation of the eye bottom up to a tooth-like line, gonioscopy, detection of minute variation of eye structures under observation and spatial-depth localization of pathologic structures are provided.

Many other modifications of the Goldman gonioscope are known.

The inventor herein has developed a Gorldman-type gonioscope that is described in U.S. Pat. No. 6,942,343 issued on Sep. 13, 2005. This gonioscope comprises a hollow tapered body with mirror surfaces formed on the inner side of the gonioscope or on the inner surfaces of the inserts which are placed into the recesses on the inner surface of the gonioscope. Several reflecting surfaces can be arranged at the same or different angles to the longitudinal axis of the gonioscope. In the second embodiment, the gonioscope can be made disposable and molded with reflecting surface applied after molding onto the inner flats by evaporation in vacuum, or by other methods. In a third embodiment the gonioscope is used in combination with a double-concave contact lens which is applied onto the eye cornea and is attached to or is separate from the gonioscope body and is used as a support for sliding the front end of the gonioscope over the lens surface for orientation thereof at different angles to the optical axis of the eye. In a fourth embodiment, the gonioscope is an assembly of the tapered body with the mirror inserts placed into the recesses on the inner surface of the hollow gonioscope.

However, the aforementioned gonioscope is intended only for intraocular observations and diagnostics. On the other hand, optical methods and devices find application not only for observation and diagnostics, but also for eye treatment and surgery. An advantage of such methods and devices is that they make it possible to treat an eye not only on its surface but also in an intraocular manner without destruction of the eye cornea. One of the most popular and well developed techniques of optical eye surgery is intraocular laser surgery.

The main part of the eye is composed of light-transmitting and light-refracting media that make it possible to deliver a light beam to any internal part of the eye.

At the present time, about 95% of surgical operations used in ophthalmology are performed with the use of laser eye surgery.

Presently, laser ophthalmology utilizes almost the entire color spectrum of lasers and allows for treatment of all elements of the eye structure. For example, the 1.9–2 μm infrared lasers or ytterbium-erbium lasers effectively act on the eye cornea and are used in operations aimed at elimination of astigmatism and farsightedness up to 4–5 diopters.

Ultraviolet lasers, e.g., excimer lasers, can be used for dosed thinning of the cornea thus reducing its refracting power for elimination of shortsightedness up to 8–12 diopters and astigmatism. They also make it possible to perform keratoplasty under outpatient conditions, to treat initial stages of keratoconus, to ablate surface layers of the cornea damaged by keratoluekoma, etc.

Visible beam lasers makes it possible to "touch-up" the marginal ring ulcer of the cornea for sanitation purposes, efficiently eliminate infections in the ulcer of the cornea, eliminate virus in the cornea, delete neoplasmic vessels in the cornea, etc. Furthermore, the lasers are used for non-invasive destruction of cysts and tumors in the anterior chamber of the eye, formation of eye pupils, correction and displacement of the eye pupils, elimination of synechias, closing of vessels in the iris of the eye, elimination of hyphemia, removal of sutures from the cornea, etc.

The use of gonioscopes for intraocular laser surgery is known. For example, U.S. Pat. No. 4,728,183 to Heacock issued in 1988 describes an indirect ophthalmology contact lens device that utilizes a contact lens element situated relative to an entry lens in a holder. It is stated that the contact lens element is designed such that the light rays emerging from the patient's eye exit the contact lens in a parallel relationship which are then directed to the entry lens. The entry lens is an aspheric lens which forms an aerial image of the fundus. This patent thus describes an ophthalmic lens system wherein the contact lens has two spherical surfaces, designed such that light rays emerging from the patient's eye and through the contact lens are substantially parallel, rather than convergent, as they exit in an anterior direction from the contact lens. In this design, the aspheric entry lens of this invention will be inadequate in some circumstances as an image forming lens as it will be insufficient for correcting field curvature and aberrations due in part to the spherical design of the contact lens. The contact lens design has failed to account for the corrective quality of the aspheric cornea of the eye itself and may tend to degrade the image of the fundus of the eye. It is also desired to form an extremely wide field image of the fundus of the eye using a diagnostic contact lens system to enable the ophthalmologist and optometrist to view more of the fundus for proper and easier diagnosis. In the invention of Heacock as well as other prior art inventions, mirrors are sometimes interposed between the contact lens and entry lens of the system to increase the field of view of the fundus. The addition of mirrors into the system adds complexity, costs and may tend to degrade the quality of the image. Even with the use of mirrors it may still be necessary to move the lens on the examined eye. In a similar manner, the indirect ophthalmoscopy diagnostic contact lens system should function as a condensing lens for converging light from the light source of a biomicroscope through the pupil of an examined eye onto the fundus of the eye. In order to obtain an aberration free, focused image of the light source, such as in a slit lamp biomicroscope or other ophthalmoscope, the lens system should provide the optical properties to avoid aberrations normally associated with spherical lenses.

An attempt to eliminate the above disadvantages is disclosed in U.S. Pat. No. 5,046,836 issued to D. Volk in 1991. This invention relates to a compound diagnostic indirect ophthalmoscopy contact lens utilized for illumination and observation of the fundus of the eye including a plus powered meniscus aspheric contact element and a biconvex aspheric anterior element, each of the lens elements contributing positive refractive power to the optical system and co-acting to illuminate and form an aerial image of the fundus of the eye. One of the objects of the Volk's invention is laser delivery to the far peripheral as well as the central fundus of an examined eye.

U.S. Pat. No. 5,347,326 issued to D. Volk in 1994 describes a gonioscope-type laser treatment of the eye of a patient. The diagnostic or therapeutic contact lens comprises a lens body, constructed of a rigid, transparent material, and includes a concave posterior surface to be selectively positioned on the cornea of an eye. The posterior surface will preferably have a curvature substantially conforming to the curvature of the cornea and will be translationally movable on the cornea during observation or treatment to facilitate examination procedures. The posterior surface of the lens body may include channels for permitting the egress of air from between the posterior surface of the lens body and the surface of the cornea of the eye being examined. The channels may be located about the periphery of the optically functional portion of the posterior surface, such that air trapped in the precorneal region will be immediately displaced from the precorneal space so as to allow tear fluid of the eye to interface between the posterior surface and cornea. Subsequent to examination or treatment using the diagnostic or therapeutic contact lens, the channels for permitting the egress of air from the precorneal region will also facilitate removal of the lens from the cornea. The diagnostic or therapeutic contact lens will eliminate the need for using an ophthalmic solution in association therewith and will also substantially eliminate the creation of suction between the cornea and the contact lens.

U.S. Pat. No. 5,523,810 issued to D. Volk in 1996 discloses an indirect ophthalmoscopy contact lens device that includes a contact lens having a first posterior lens surface with a concave shape substantially corresponding to the shape of an average cornea and an image forming lens for collecting and focusing light exiting the patient's eye and entering the contact lens when in place on the patient's eye for forming an aerial image of the fundus of the patient's eye. The contact lens comprises a compound contact lens element including a posterior lens portion cemented to an anterior lens portion. The posterior lens portion includes the first posterior lens surface and a first anterior lens surface, and is made of a material having a first index of refraction and a first Abbe value. The anterior lens portion has a second posterior lens surface with a shape substantially matching a shape of the first anterior lens surface and a second anterior lens surface having a convex shape. The anterior lens portion is made of a material having a second index of refraction and a second Abbe value. At least one of the second index of refraction and the second Abbe value is different from the first index of refraction and the first Abbe value, respectively. The optical cement preferably has an index of refraction corresponding to the first or second index of refraction.

U.S. Pat. No. 5,805,269 issued to D. Volk in 1998 discloses an indirect ophthalmoscopy lens device provided for use with slit-lamps or other biomicroscopes for examination, laser treatment or surgical treatment of a patient's eye. The device comprises an image forming lens system for collecting and focusing light exiting a patient's eye to form a real image of the fundus of the patient's eye at a location outside the eye and anterior of the image forming lens system. An anterior lens having a convex anterior surface is disposed anterior to the image forming lens system so that the real image formed by the image forming lens system is located posterior of the convex anterior surface. The convex anterior surface of the anterior lens refracts chief rays of light ray bundles of the light exiting the patient's eye generally toward a collecting lens of the slit-lamp or other biomicroscope. An image viewed through the slit-lamp or other biomicroscope comprises a virtual image that has a positive magnification relative to the real image formed by the image forming lens system and relative to the fundus of the patient's eye.

US Patent Application Publication No. 20020167644 filed by I. Pollack, et al. and published on 2003 describes an iridotomy and trabeculoplasty goniolaser lens that comprises a contact lens element, a planar mirror offset from the optical axis of the contact lens element and first and second button lenses mounted on the anterior surface of the contact lens element. Magnification, curvature and location of the button lenses are chosen so as to provide the ability to simultaneously deliver laser energy to the iris of a patient's eye along a first optical path offset from the optical axis of the contact lens element and to view the trabecular meshwork around the region where the laser energy was applied. This ability eliminates the need for a plurality of contact lenses for delivering energy and viewing the eye and further eliminating the need for refocusing the microscope through which the surgeon views the eye.

Another method for relieving the symptoms of open-angle glaucoma is to perform trabeculoplasty using laser ablation surgery. This procedure is accomplished by delivering laser energy to the trabecular meshwork to allow better passage of the aqueous humor through it. One theory suggests that the laser alters the intracellular and intercellular structures in the trabecular meshwork and allows the fluids to pass through with less obstruction.

Prior contact lenses employed for these purposes work efficiently for the application of laser energy to the eye. However, viewing the trabecular meshwork before and after an iridotomy procedure has necessitated removal of the laser lens and substitution of another viewing lens. While attempts have been made at combining a laser delivery lens and a viewing lens, the attempted combinations have not been successful for a variety of reasons. The major reason for lack of success has been the necessity to completely refocus the binocular microscope through which the surgeon is manipulating the laser energy and through which the surgeon views the trabecular meshwork.

During an iridotomy procedure, it is desirable to view the trabecular meshwork immediately after the delivery of laser energy to determine the efficacy of the procedure. If the aperture through the iris has been successfully completed, fluid pressure in the posterior chamber will be relieved and will allow the iris to flatten to its natural state rather than the anteriorly bowed configuration that occurs in the presence of excessive intraocular pressure in the posterior chamber. When laser iridotomy has been mechanically successful, the anterior chamber angle will open, as observed through the gonioscopy portion of the lens. However, if it is observed that the angle failed to open, then additional application of laser energy may be required. Thus, if the anterior chamber angle and trabecular meshwork could be viewed immediately after the initial delivery of laser energy through the same contact lens, an additional application of laser energy could be applied to the same or another location without removing the laser delivery lens, without substituting the viewing lens and without once again repositioning the laser delivery lens.

U.S. Pat. No. 5,309,187 issued in 1994 to J. Crossman, et al. describes an ophthalmic lens having two elements, a contact lens and an entry lens. The lens produces a magnified aerial image of the fundus of the eye, and can also be used for laser delivery to the fundus. The lens provides high magnification and detail of the fundus as well as excellent stereoscopic field.

U.S. Pat. No. 6,767,098 issued to P. Erickson, et al. in 2004 discloses an ophthalmoscope prism, for example a gonioscope, that has an optically transparent body, the distal end carries a viewing surface preferably oriented perpendicularly to the optical axis of the body, the proximal end of the prism carries a concave surface having a curvature similar to the curvature of the cornea of a patient. The proximal end has at least one planar surface extending outwardly and distally from a location adjacent the periphery of the concave surface. The body has an index of refraction that provides total internal reflection to a viewer looking through the viewing surface even when the planar surface is at least partially wetted with a fluid.

U.S. Pat. No. 5,548,352 issued in 1996 to D. Dewey discloses a contact lens for viewing the interior of a patient's eye during an argon laser trabeculoplasty (ALT) procedure and for delivering laser energy to desired regions of the trabecular meshwork of the eye. The contact lens is fabricated from a hollow plastic body which is filled with a medium having an index of refraction which is substantially the same as that of the aqueous humor within a patient's eye. Visible and laser light enter the lens by means of a thin window of substantially uniform thickness and exit the lens (thereby entering the eye) at a front face of substantially uniform thickness whose outer curvature is approximately the same as that of the patient's eye. The degree of astigmatic focusing which normally occurs as the visible light and laser beam pass through the contact lens and cornea and into the aqueous humor is substantially reduced. This assists the surgeon performing the procedure to better view the interior of the eye and to place a better defined laser spot on the desired regions of the trabecular meshwork.

U.S. Pat. No. 5,841,510 issued in 1998 to D. Roggy describes a lens device for examining portions of the human eye comprising inner and outer members each having opposed end portions, the outer member having a viewing lens adjacent one end portion thereof, the inner member being rotatably mountable within the outer member and having at least one mirror associated therewith, the at least one mirror being located adjacent the viewing lens when the inner member is positioned within the outer member, the inner member being rotatably movable relative to the outer member such that the at least one mirror can be selectively positioned relative to the viewing lens so that the appropriate area of the eye can be examined. Preferably, the inner member is rotatable a full 360 DEG while the outer member remains stationary adjacent a patient's eye and, preferably, the inner member includes a plurality of circumferentially spaced mirrors. Although the present device is particularly adaptable for use in association with a wide variety of diagnostic lens such as gonioscopy and/or fundoscopic lens, the present device is likewise equally adaptable for use in many other eye lens applications including lenses used in laser treatment and/or surgery of the eye.

U.S. Pat. No. 5,252,998 issued in 1993 to W. Reis discloses an instrument for the examination and/or laser treatment of the eye having an examination device designed for the examination of the fundus oculi and having a contact eyeglass, which is provided with a lens which can be placed on the eye, the eye-facing surface of the lens being adapted to the curve of the cornea. The lens which is placed on the eye has no spherical power at least in the region of the optical axis.

Russian Patent No. RU 2125426, issued on Jan. 27, 1999 to V. A. Egorov, et al., described a laser treatment of glaucoma and relates to a method that involves making intervention in the form of otomydriasis, gonioplasty and trabeculoplasty by means of laser radiation on copper vapor. Radiation pulses are 10–30 ns long at two wavelengths of 511 nm being green component and 578 nm being yellow one. Ratio of green and yellow components power belongs to the interval of 1:1 to 1:2.5. Mean power of radiation is equal to 0.1–0.5 W. Pulse repetition frequency is equal to 10–30 Hz, exposition time is 0.1–0.5 s, light spot diameter is equal to 100–500 mcm. The method provides a controlled action in required zone of the anterior eye interval.

A common disadvantage of the known laser gonioscopes equipped with contact lenses for supporting the gonioscope on the patient's eye is inefficient delivery of laser and illumination beams and the use of complicated optical systems for delivery of beams. This is because design of known contact lenses of laser gonioscopes cannot provide conditions needed for effective delivery of both laser and illumination beam through the body of the lens. Furthermore, the use of a combined observation and/or laser gonioscopy on a contact lens that is disconnected from the gonioscope body and serves as a guiding support for sliding the body over the surface of the lens is unknown.

Another common disadvantage of the known gonioscope systems utilizing contact lenses is that the conventional contact lenses used as a support of the gonioscope bodies are inconvenient to handle and may require the use of a special instrument for putting into patients' eyes. Furthermore, in a majority of operations, especially those associated with observation and treatment, e.g., of glaucoma, the light beams pass at an acute angle mostly via an edge portion of the contact lens while the central part of the contact lens remains optically unused.

SUMMARY OF THE INVENTION

It is an object of the present invention to provide a gonioscope suitable for both intraocular laser surgery and diagnostic observation, which is equipped with a contact lens for supporting the gonioscope on the patient's eye and provides efficient delivery of laser and illumination beams through a simplified optical system. It is another object to provide a soft contact lens of a laser surgery/diagnostic gonioscope system that has a design suitable for efficient delivery of both laser and illumination beams through the body of the lens. It is another object to provide a gonioscope/contact lens system that incorporates a set of replaceable soft contact lenses having different structures and optical characteristics for versatile use of the gonioscope. It is another object to provide a gonioscope/contact lens system with a contact lens having a composite structure consisting of a rigid main optical portion and a soft eye-contact optical coating. It is another object to provide a gonioscope for laser with a soft contact lens disconnectable from the gonioscope body and serving as a guiding support for sliding the body over the surface of the lens in the lateral direction. It is another object of the invention to provide a gonioscope-lens system where the soft contact lens has a tail portion that facilitates handling of the lens and where the central part of the lens may be actively used for passing optical beams.

The invention is applicable to gonioscopes with contact lenses rigidly attached to the gonioscope body as well as to gonioscopes having a mirror cone body guided over an independent contact lens. According to one embodiment of the invention, the gonioscope/contact lens of the invention has a contact lens in a mushroom shape with the cap of the "mushroom" (hereinafter referred to as the lens head) having a concave surface on the front side of the lens corresponding to the curvature of the eye, onto which the lens is to be placed, and a "mushroom" stem (hereinafter referred to as a lens tail portion) that extends in the direction opposite to the patient's eye. The tail portion is connected to the lens head by a tapered side surface with a circular shoulder on the edge of the tapered portion for supporting the gonioscope body on the lens. The following modifications are possible: 1) a concave end face of the lens tail portion is used for guiding a collimated illumination beam from above towards the eye in the direction of the optical axis of the lens; the pointing and power laser beams are incident on the respective mirrors on the inner surface of the gonioscope body and guided into the eye through flat surface areas formed on the aforementioned tapered portion; 2) a convex end face of the lens tail portion is used for guiding converging laser beams onto the area of interest of the eye from above in the direction of the optical axis of the lens; one mirror on the inner surface of the gonioscope body is used for directing an illumination beam through a flat surface area formed on the aforementioned tapered portion; another mirror may be used for observation; 3) a convex lens formed on the tapered portion of the lens is used for guiding and focusing a collimated laser beam reflected to this lens from a mirror on the inner surface of the gonioscope body, while a concave lens formed in another location on the same tapered portion is used for guiding and diverging an illumination beam reflected onto this lens from another mirror on the inner surface of the gonioscope body. Other modifications are possible with lenses for lasers and illumination beams located on the rear end of the gonioscope body instead of the flat end face of the lens tail. A combination of lenses of different shapes with flat surfaces on the tapered portion makes it possible to provide the most efficient delivery of the beams to the area of interest on the cornea or inside the patient's eye. In the gonioscope-lens system of the invention, the tail portion of the contact lens facilitates handling of the lens, and the central part of the lens may be actively used for passing optical beams.

According to another embodiment, the contact lens does not necessarily have a mushroom shape with a tail portion and may consists of a front eye-contact lens portion and a rear main optical portion of any arbitrary shape, provided that this optical portion has flat surfaces arranged perpendicular to the beams reflected from the reflecting mirrors of the gonioscopic body. In a preferred embodiment, the rear optical portion has a prismatic shape with flat sides of the prism. Alternatively, the rear optical portion may have a conical shape with flats on the conical surface. The entire contact lens may have a monolithic structure and made from a soft biocompatible plastic material such as soft acrylic or polyurethane. According to another modification, the main optical part of the contact lens can be made of a rigid optical material such as glass that provides high dimensional accuracy while the portion of the lens that is intended for contact with the cornea of the patient's eye is made of a soft plastic coating or insert attached to the front side of the rigid part of the lens. Disposable may be the entire optical lens or the insert that can be connected to the rigid part via a wetting gel.

DETAILED DESCRIPTION OF THE INVENTION

Figure 1:
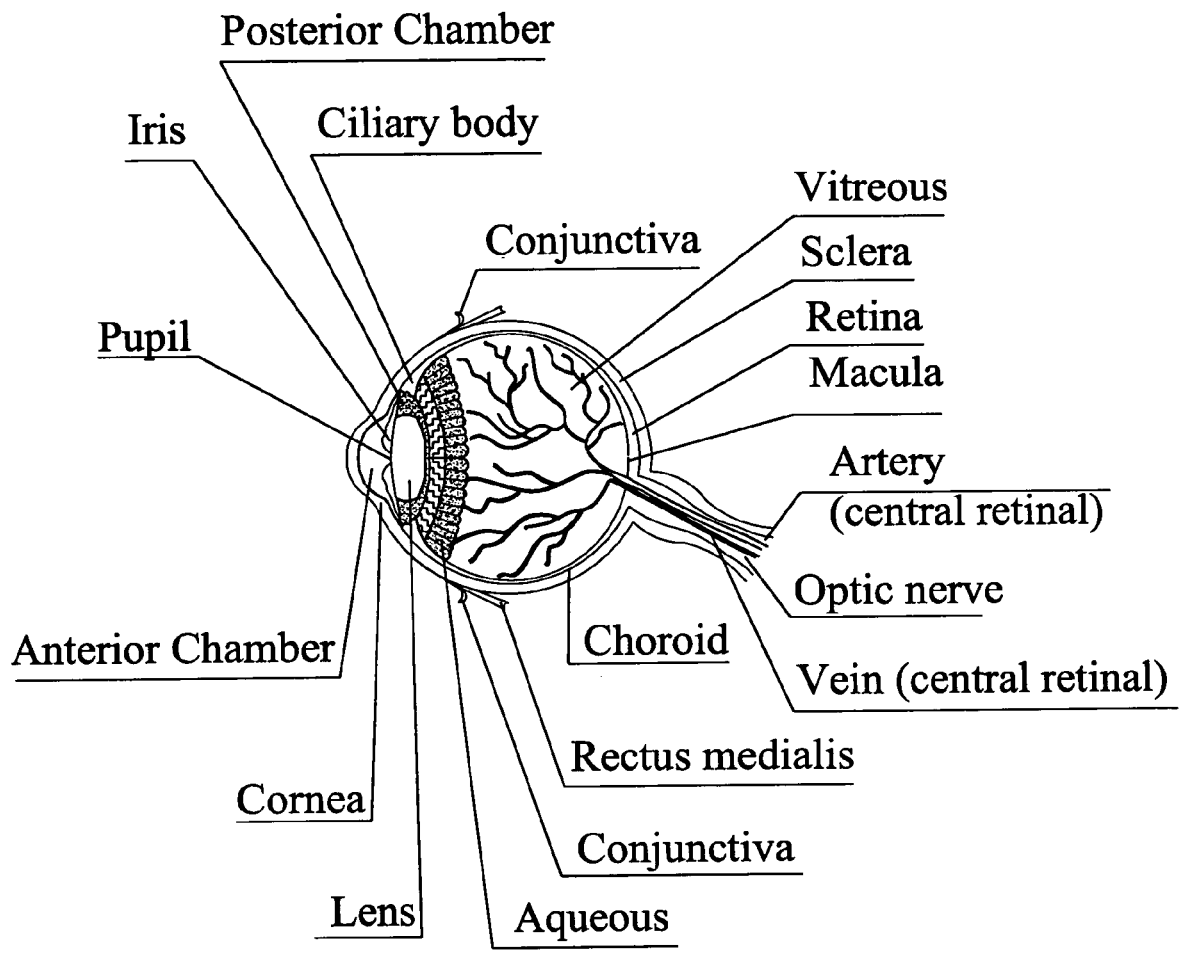
FIG. 1 is a cross-sectional view of a human eye.
Figure 2:
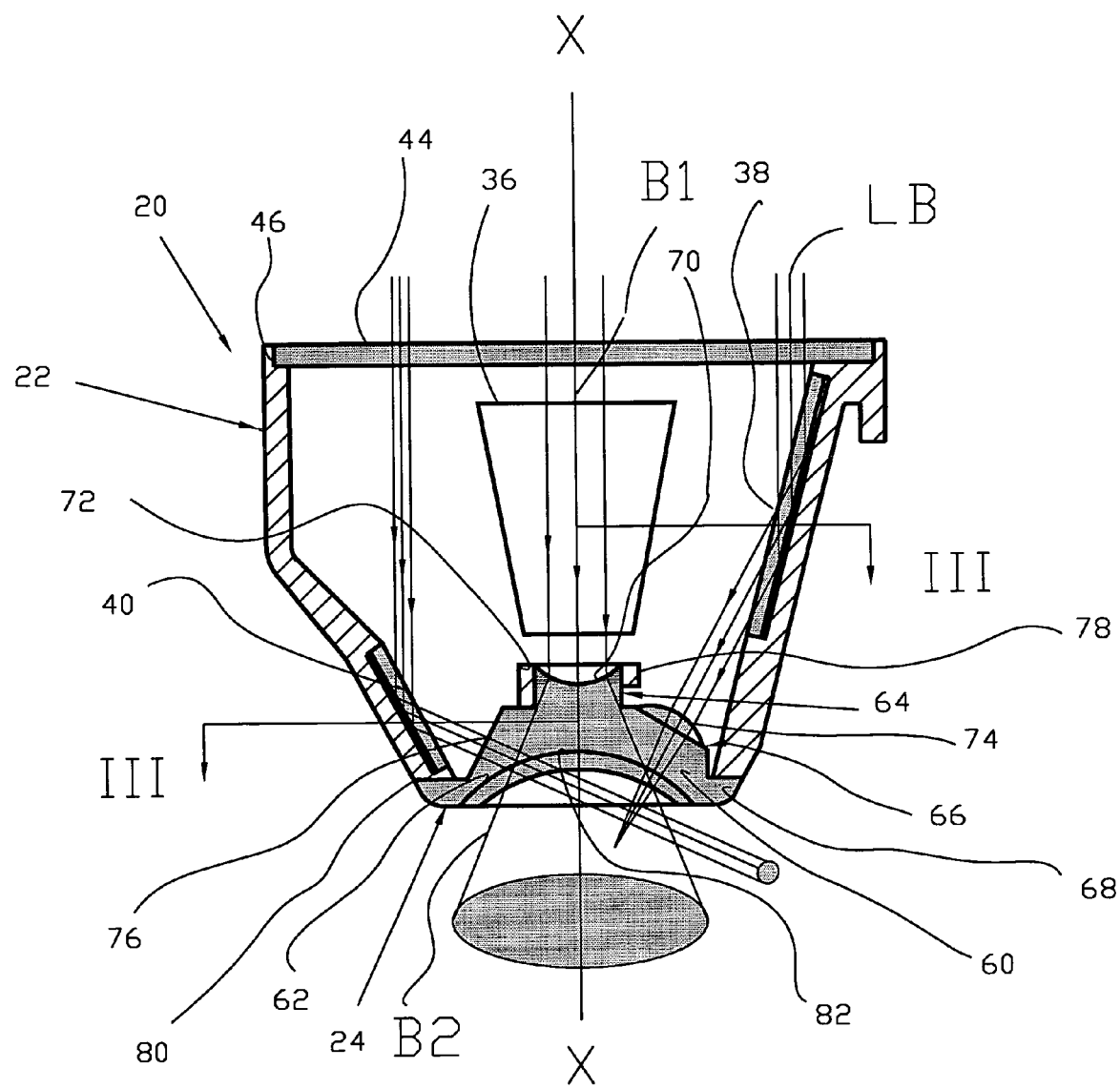
FIG. 2 is a longitudinal cross-sectional view of a universal gonioscope-lens system made in accordance with one embodiment of the invention.

As shown in FIG. 2, which is a longitudinal cross-sectional view of the universal gonioscope—contact lens system (hereinafter referred to as "gonioscope-lens system) made in accordance with one embodiment of the invention, the system 20 consists mainly of two major elements, i.e., a hollow tapered body 22 with mirror surfaces (which are described later) formed on the inner side of the gonioscope body 22 and a contact lens 24 of a specific shape which is applied onto the eye cornea (not shown). In the embodiment of FIG. 2, the contact lens 24 is made as a part separate from the gonioscope body 22 and used as an optical element of the system 20 and as a support for the freely interchangeable different gonioscope bodies such as the body 22 that can be used for different purposes, e.g., for observation, for laser surgery, for changing optical angles of the system, etc. The aforementioned main optical elements of the system 20, i.e., the gonioscope body 22 and the contact lens 24, will now be considered in detail separately.

A hollow gonioscope body 22 has a substantially tapered shape and can be molded from a biocompatible plastic. Examples of such plastics are the following: polycarbonate, acrylic, or the like. Preferably, the side walls of the body 22 are made non-transparent to light.

Figure 3:
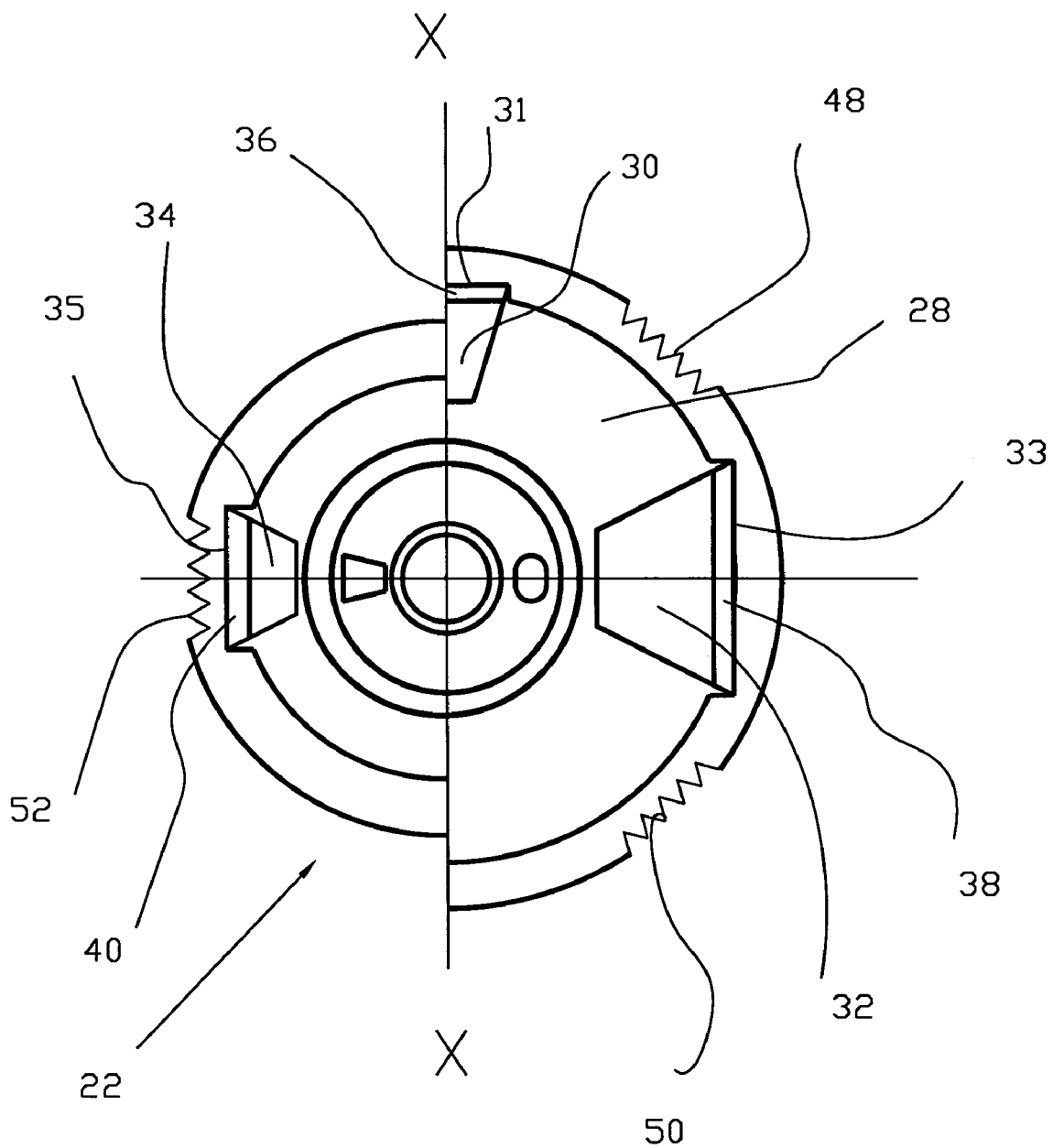
FIG. 3 is a cross-sectional view of the gonioscope body along the line III—III of FIG. 2.

FIG. 3 is a cross-sectional view of the gonioscope body 22 along the line III—III of FIG. 2. The inner surface 28 of the body 22 has at least one, but preferably a plurality of recesses 31, 33, 35 (FIG. 3). It is understood that three recesses are shown as an example and that their number may be less or greater than three. The recesses 31, 33, 35 accommodate reflection mirror inserts 36, 38, 40, respectively, with the mirror surfaces 30, 32, and 34 (FIG. 3) formed, e.g., by mirror metal coatings formed on the inner sides of the mirror inserts so that the mirror surfaces are not exposed to the cavity of the hollow gonioscope body 22 (FIGS. 2 and 3) and thus protected from damage during cleaning. The aforementioned mirror surfaces are inclined at an acute angle with respect to the optical axis X—X of the gonioscope-lens system 20. In order to diminish the effect of double refraction, the mirror inserts are made from thin transparent glass plates with mirror surfaces on the inner side of the insert, i.e., on the side facing away from cavity of the hollow gonioscope body 22.

Figure 4:
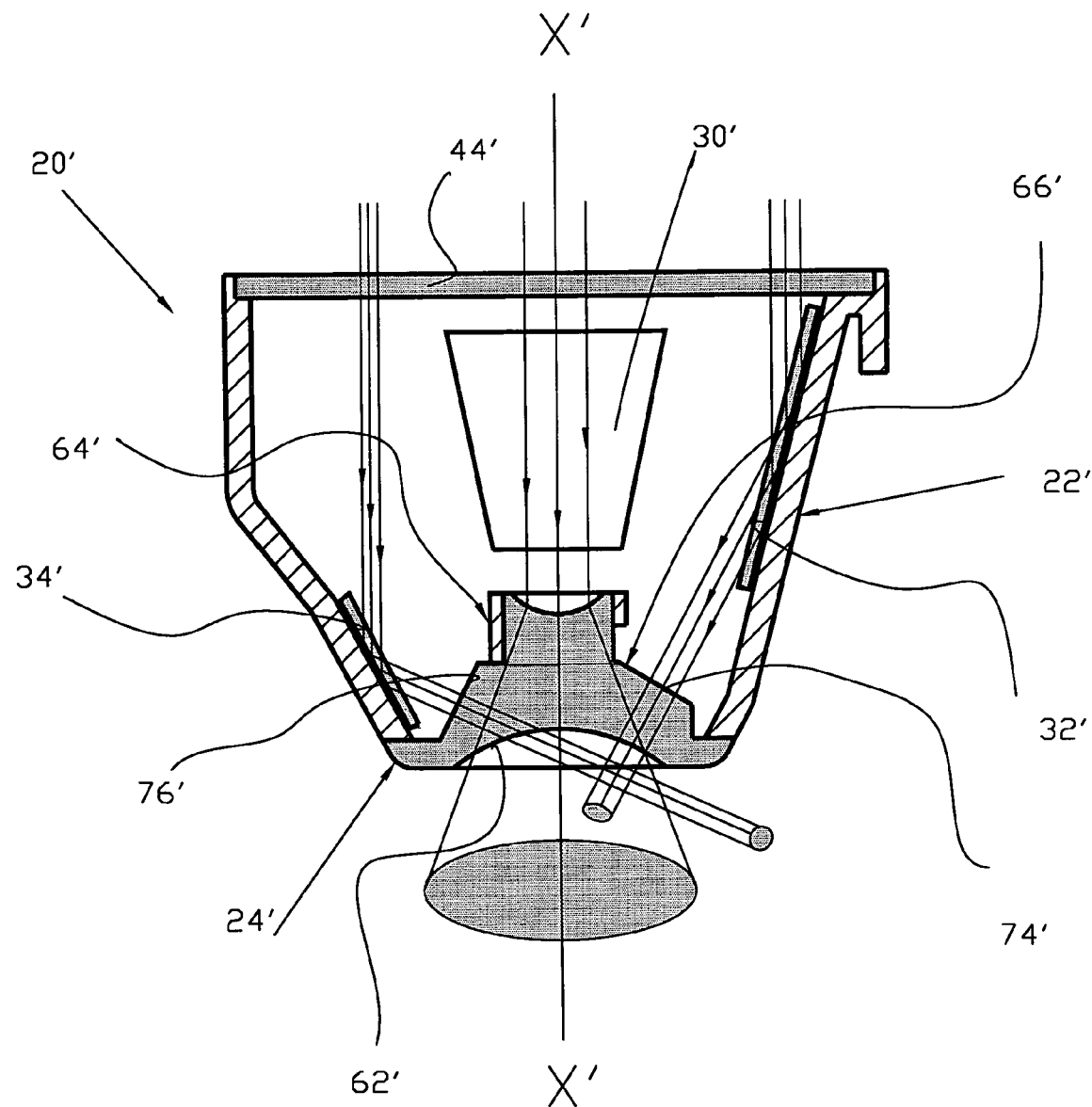
FIG. 4 is a longitudinal sectional view of a gonioscope body similar to the one shown in FIG. 2 but with the mirror coating formed directly on the inner side of the hollow body without the use of mirror inserts.

As shown in FIG. 4, which is a longitudinal sectional view of a gonioscope body 22' according to another embodiment, the mirror surfaces can be formed directly on the inner side of the hollow body 22' without the use of mirror inserts but applying the mirror coatings 30', 32', and 34' onto flats or specifically profiled surfaces formed in the inner side of the body 22'. Another difference is that a flat area 74' is formed on the tapered portion 66' instead of the convex lens 74. The other features of the gonioscope of FIG. 4 are the same as those shown in FIG. 3 and therefore do not need a detailed description.

Reference numeral 44 (FIG. 2) designates a protective glass cover installed in a recess 46 on the large-diameter side of the gonioscope body 22. The use of the glass cover 44 is optional. Another optional feature that can be used for convenience of grasping and holding is formation of flats 48, 50, and 52 (FIG. 3) on the outer tapered portion of the body 22. The surfaces of the flats 48, 50, and 52 may be roughened for increase of the friction coefficient.

The mirror inserts 36, 38, 40 may be replaced for changing the functions of the gonioscope between purely observational or observational and laser surgical.

In the embodiment shown in FIG. 2, the mirror insert 40 can be used for observation of the area of interest inside the eye, and the mirror insert 38 can be used for delivery of the laser beam LB.

The contact lens 24 has a mushroom shape with the cap 60 of the "mushroom" (hereinafter referred to as the lens head) having a concave surface 62 on the front side of the lens corresponding to the curvature of the eye (not shown), onto which the lens 24 is to be placed, and a "mushroom" stem 64 (hereinafter referred to as a lens tail portion) that extends in the direction opposite to the patient's eye. The tail portion 64 is connected to the lens head by a tapered portion 66 with a circular shoulder 68 on the edge of the tapered portion 66 for supporting the gonioscope body 22 on the lens 24.

In the embodiment shown in FIG. 2, the contact lens 24 has a concave lens 70 formed on the rear end face 72 of its tail portion 64. This lens 70 is used for guiding a collimated illumination beam B1 directed from an illumination light source (not shown) towards the eye (not shown) in the direction of an optical axis X—X of the lens 24 (FIG. 2). As shown in the drawing, the beam B1 is diverged by the lens 70 and is emitted from the contact lens through its front concave surface 62 in the form of a diverging beam B2 to illuminate the inner part of the eye (not shown).

As shown in FIG. 2, the contact lens 24 has a convex lens 74 formed on a part of its tapered portion 66, and a flat area 76 formed in another location on the tapered portion 66. The concave lens serves for focusing the laser beam LB directed from a laser source (not shown) and reflected towards the convex lens 74 from the mirror surface of the mirror insert 38 (FIGS. 2 and 3), while the flat area 76, which is perpendicular to the direction of the beam reflected from the mirror 33 (FIG. 3) of the insert 38 and is intended for passing the aforementioned illumination light beam B2.

The entire surface of the contact lens, except for areas occupied by the concave lens 70, convex lens 74, and front concave surface 62, is coated with a light-impermeable coating (nor shown) that may be applied, e.g., by sputtering. If necessary, instead of a coating with a light-impermeable coating, a thin light-impermeable sleeve 78 may be fitted onto the tail portion 64 (FIG. 2).

In the system 20 of FIG. 2, the contact lens 24 serves as an optical element and as a support for the hollow conical body 22 of the gonioscope that rests with its front end face 80 on the shoulder 68 of the contact lens 24.

If necessary, the concave surface 62 of the contact lens 24 can be formed on a layer 82 that is attached to the front face of the contact lens 24 and is made from a material softer than the body of the contact lens 24.

In operation, e.g., for examination, diagnosing conditions, and/or performing a laser operation on the retina of the eye (not shown), the contact lens 24 is gently placed with its concave surface 62 on the cornea of the eye after appropriate therapeutic procedures, such as anesthesia, application of a cushioning agent, etc., which are beyond the scope of the present invention. The mirror surface of the mirror insert 40 (FIGS. 2 and 3) is illuminated by a light beam B2 from an external light source (not shown). The beam B2 is reflected from the mirror surface of the insert 40 and illuminates, e.g., the retina, in the area remote from the optical axis of the eye (not shown).

Generally speaking, illumination of the areas to which the beam B2 is incident occurs in a certain solid angle which depends on the inlet aperture of the eye pupil. The light incident on the retina is scattered and illuminates the entire inner cavity of the eye.

Various inner potions of the eye retina, which are illuminated with the external light, in turn, emits secondary light which can be seen through the eye pupil (not shown) and mirror surfaces such as the mirror surface of the insert 40. Depending on the angle of observation and the selected mirror, the ophthalmologist can see various portions of the retina, including those remote from the optical axis of the eye.

By manipulating the gonioscope body 22 together with the contact lens 24 on the eye cornea, the ophthalmologist can see various peripheral areas inside the eye, e.g., the anterior.

At the same time, the mirror surface 33 (FIG. 3) of the insert 38 is used for reflecting a laser beam LB onto the convex surface of the lens 74. The latter focuses the beam LB onto the area of interest inside the patient's eye for performing a required operation in accordance with the procedure known in the art.

The device shown in FIG. 4 operates in the same manner with the exception that mirror surfaces 30', 32', and 34' of the gonioscope are formed directly on the inner side of the body 22' instead of the inserts that are not used in the embodiment of FIG. 4. One of the flats, e.g., the flat 74' may be used for beams different from those reflected by the mirror 34'.

Figure 5:
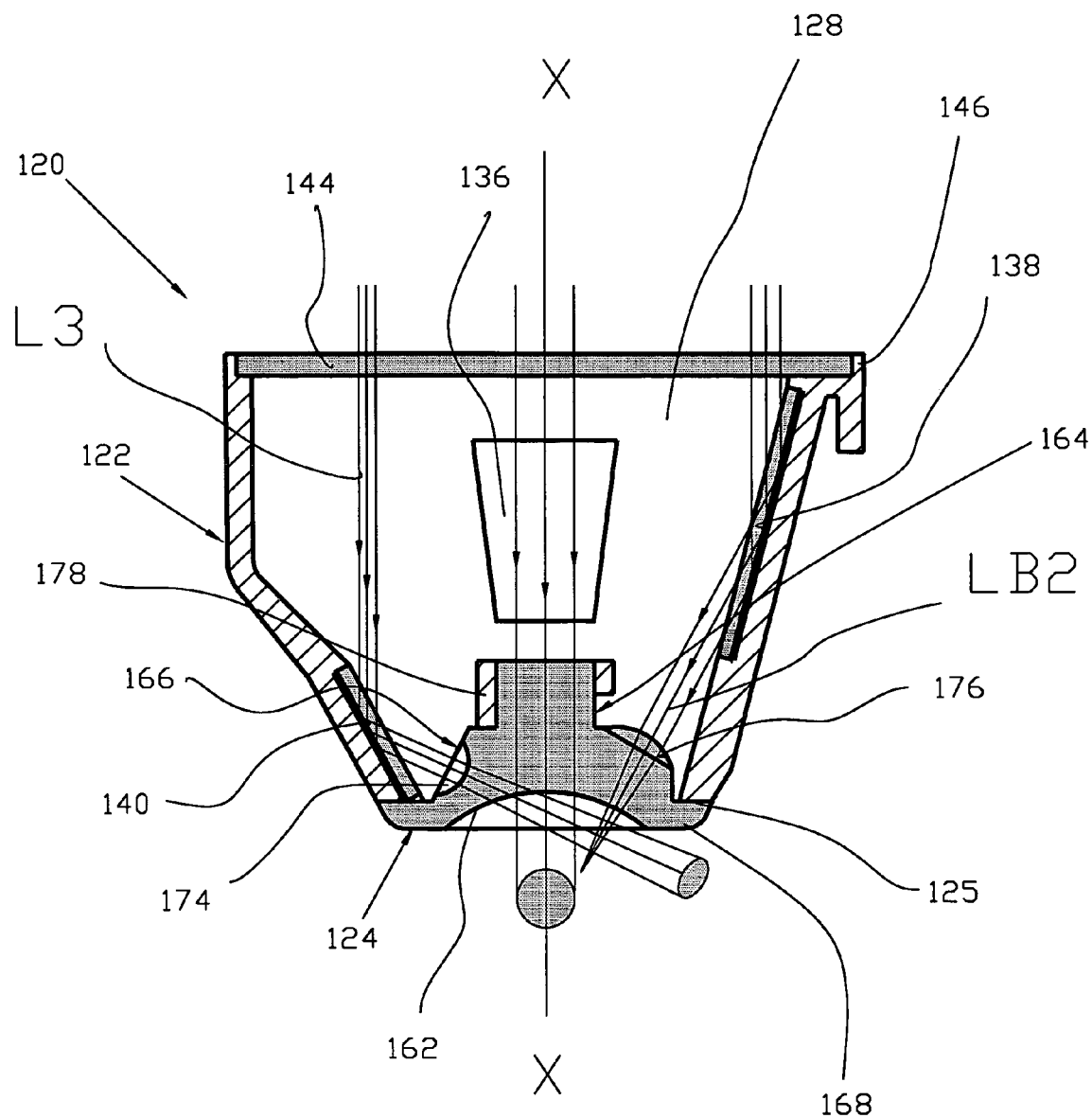
FIG. 5 is a longitudinal cross-sectional view of the universal gonioscope-lens system made in accordance with a further embodiment of the invention, wherein the laser delivery lens and the illumination light lens are formed on the tapered side surface of the contact lens, the gonioscope body being cemented to the contact lens.

FIG. 5 is a longitudinal cross-sectional view of the universal gonioscope-lens system 120 made in accordance with another embodiment of the invention. Since the system 120 is similar to the system 20 described above with reference to FIGS. 2–4, the parts of the system 120 similar to those of the system 20 will be designated by the same reference numerals with an addition of 100. Thus, the gonioscope-lens system 120 consists mainly of two major elements, i.e., a hollow tapered body 122 with mirror surfaces formed on the inner side of the gonioscope body 122 and a contact lens 124 of a specific shape which is applied onto the eye cornea (not shown). In the embodiment of FIG. 5, the contact lens 124 is made as a part rigidly attached, e.g., cemented at the end face 125 to the front end face of the gonioscope body 122 and used as an optical element of the system 120 and as a support portion for supporting the gonioscope-lens system 120 on the patient's eye (not shown).

A hollow gonioscope body 122 has a substantially tapered shape and can be molded from a biocompatible plastic. Examples of such plastics are the following: polycarbonate, acrylic, or the like. Preferably, the side walls of the body 122 are made non-transparent to light.

The hollow gonioscope body 122 has the same cross-sectional view as the one shown in FIG. 3, and therefore this view and description thereof is omitted from the specification. The inner surface 128 of the body 122 may support mirror inserts 136, 138, and 140 (FIG. 5). if necessary, similar to the embodiment of FIG. 4, mirror coatings (not shown) can be formed directly on the inner surface of the gonioscope body 124.

Reference numeral 144 (FIG. 5) designates a protective glass cover installed in a recess 146 on the large-diameter side of the gonioscope body 122. The use of the glass cover 144 is optional. Another optional feature that can be used for convenience of grasping and holding is formation of flats such as flats 48, 50, and 52 (FIG. 3) on the outer tapered portion of the body 122 (not shown in FIG. 5). The mirror inserts 136, 138, and 140 may be replaced for changing the functions of the gonioscope between purely observational or observational and laser surgical.

In the embodiment shown in FIG. 5, the mirror insert 138 may serve for delivery of the laser beam LB2 onto a convex lens 176 formed on the tapered portion 166 of the contact lens 124 for focusing the laser beam LB2 onto the that zone of interest in the patient's eye (not shown). On the other hand, a concave lens 174 is formed in another area of the tapered portion 166 of the optical lens for diverging the illumination light L3 of a light source (not shown) incident on the mirror surface of the mirror insert 140 and reflected onto the lens 174. The diverged illumination light illuminates the zone of interest in the eye. Another mirror insert 136 (FIG. 5) can be used for observation.

In the embodiment of FIG. 5, the contact lens 124 is cemented at its shoulder 168 to the front end face of the gonioscope body 122.

The entire surface of the contact lens, except for areas occupied by the convex lens 176, concave lens 174, and front concave surface 162, is coated with a light-impermeable coating (not shown) that may be applied, e.g., by sputtering. If necessary, instead of a coating with a light-impermeable coating, a thin light-impermeable sleeve 178 may be fitted onto the tail portion 164.

In operation, the gonioscope-lens system 120 may be used as the system 20, but the laser beam LB2 will be directed onto the mirror insert 138 and focused by the convex lens 176, while the illumination light will be diverged by the concave lens 174. Observation will be carried out through the mirror insert 136.

Figure 6:
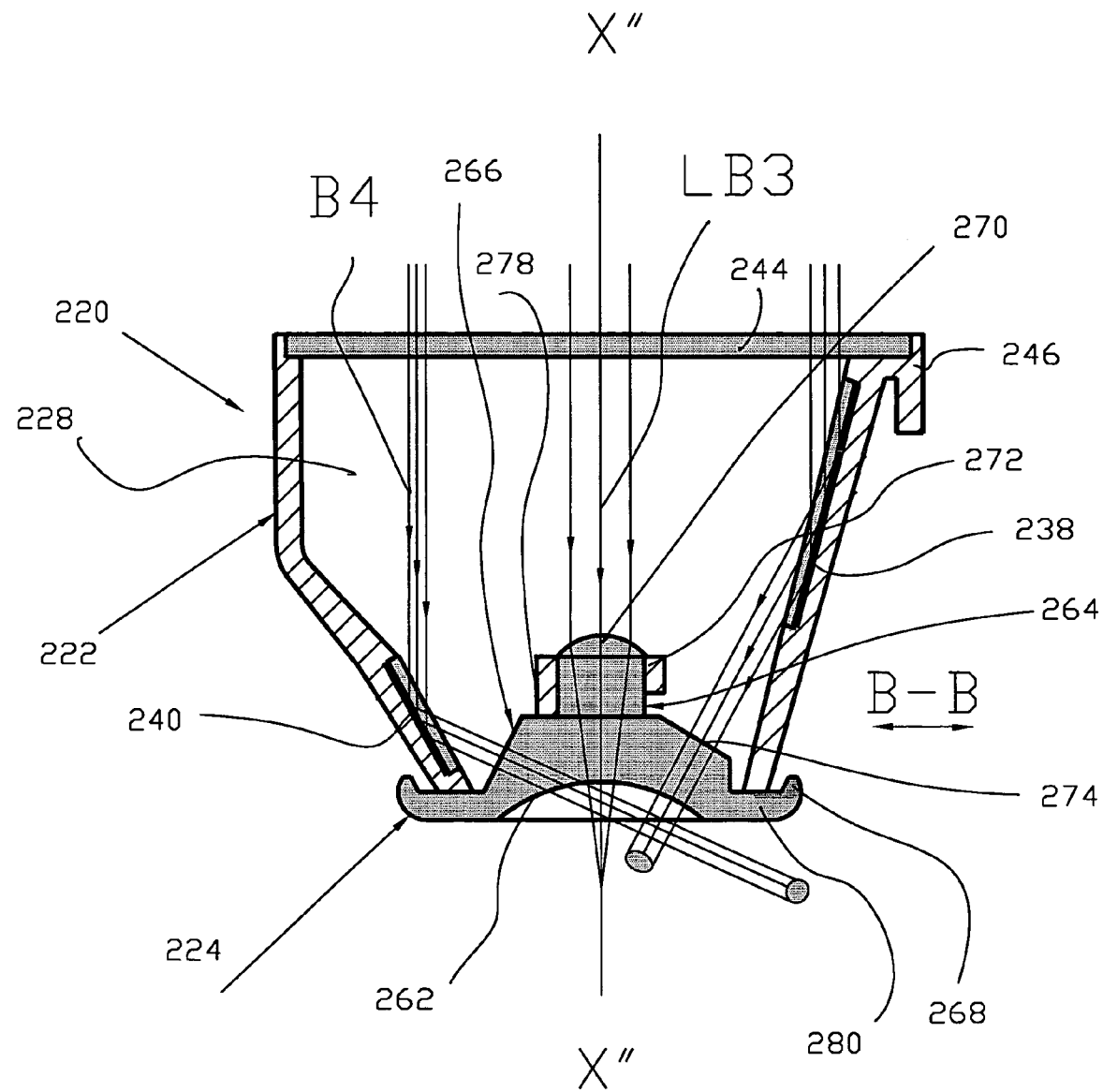
FIG. 6 is a longitudinal cross-sectional view of the universal gonioscope-lens system made in accordance with a further embodiment of the invention, wherein the laser delivery lens is formed on the back end face of the tail portion of the contact lens and wherein the contact lens serves as a support and guide for lateral movements of the gonioscope body.

FIG. 6 is a longitudinal cross-sectional view of the universal gonioscope-lens system 220 made in accordance with still another embodiment of the invention. Since the system 220 is similar to the system 20 described above with reference to FIGS. 2–4, the parts of the system 220 similar to those of the system 20 will be designated by the same reference numerals with an addition of 200. Thus, the gonioscope-lens system 220 consists mainly of two major elements, i.e., a hollow tapered body 222 with mirror surfaces formed on the inner side of the gonioscope body 222 and a contact lens 224 of a specific shape which is applied onto the eye cornea (not shown). In the embodiment of FIG. 6, the contact lens 224 is made as a part separate from the gonioscope body 222 and serves not only as an optical element of the system 220 but also as a support and guide element for the gonioscope body 222. More specifically, the support surface formed on the lens 224 for gonioscope body 222 by an annular shoulder 268 is wider than the front end face 280 of the gonioscope body 222 that rests on the surface of the shoulder. This allows for lateral movements of the gonioscope body 222 in the transverse direction B—B relative to the optical axis X'—X' over the surface of the shoulder 268 while the contact lens 224 is kept stationary on the patient's eye (not shown). The gonioscopic system 220 of this type is less traumatic for the patient's eye.

A hollow gonioscope body 222 has a substantially tapered shape and can be molded from a biocompatible plastic which is allowed for contact with the cornea of the eye. Examples of such plastics are the following: polycarbonate, acrylic, or the like. Preferably, the side walls of the body 222 are made non-transparent to light.

The hollow gonioscope body 222 has the same cross-sectional view as the one shown in FIG. 3, and therefore this view and description thereof is omitted from the specification. The inner surface 228 of the body 224 may support mirror inserts, only two of which 238 and 240 are shown in FIG. 6. if necessary, similar to the embodiment of FIG. 4, mirror coatings (not shown) can be formed directly on the inner surface of the gonioscope body 224.

Reference numeral 244 (FIG. 6) designates a protective glass cover installed in a recess 246 on the large-diameter side of the gonioscope body 222. The use of the glass cover 244 is optional. Another optional feature that can be used for convenience of grasping and holding is formation of flats such as flats 48, 50, and 52 (FIG. 3) on the outer tapered portion of the body 222 (not shown in FIG. 6). The mirror inserts 236, 238 may be replaced for changing the functions of the gonioscope between purely observational or observational and laser surgical.

In the embodiment shown in FIG. 6, the mirror insert 240 may serve for reflecting an illumination light beam B4 of a light source (not shown) and for reflecting the illumination light beam onto the zone of interests in the patient's eye through the body of the contact lens 224. The mirror insert 238 may be used for the purposes of observation.

In this embodiment, a laser beam LB3 is delivered to the zone of interest through a convex lens 270 formed on the rear end face 272 of the tail portion 264 of the contact lens 224.

The entire surface of the contact lens, except for areas occupied by the convex lens 270, the front concave surface 262, and mirror inserts, is coated with a light-impermeable coating that may be applied, e.g., by sputtering. If necessary, instead of a coating with a light-impermeable coating, a thin light-impermeable sleeve 278 may be fitted onto the tail portion 264.

In operation, the gonioscope-lens system 220 may be used as the system 20, but the laser beam LB2 will be directed onto the convex lens 270, the illumination light will be directed to the zone of interest by the mirror insert 240, while the mirror insert 238 will be used for observation.

Figure 7:
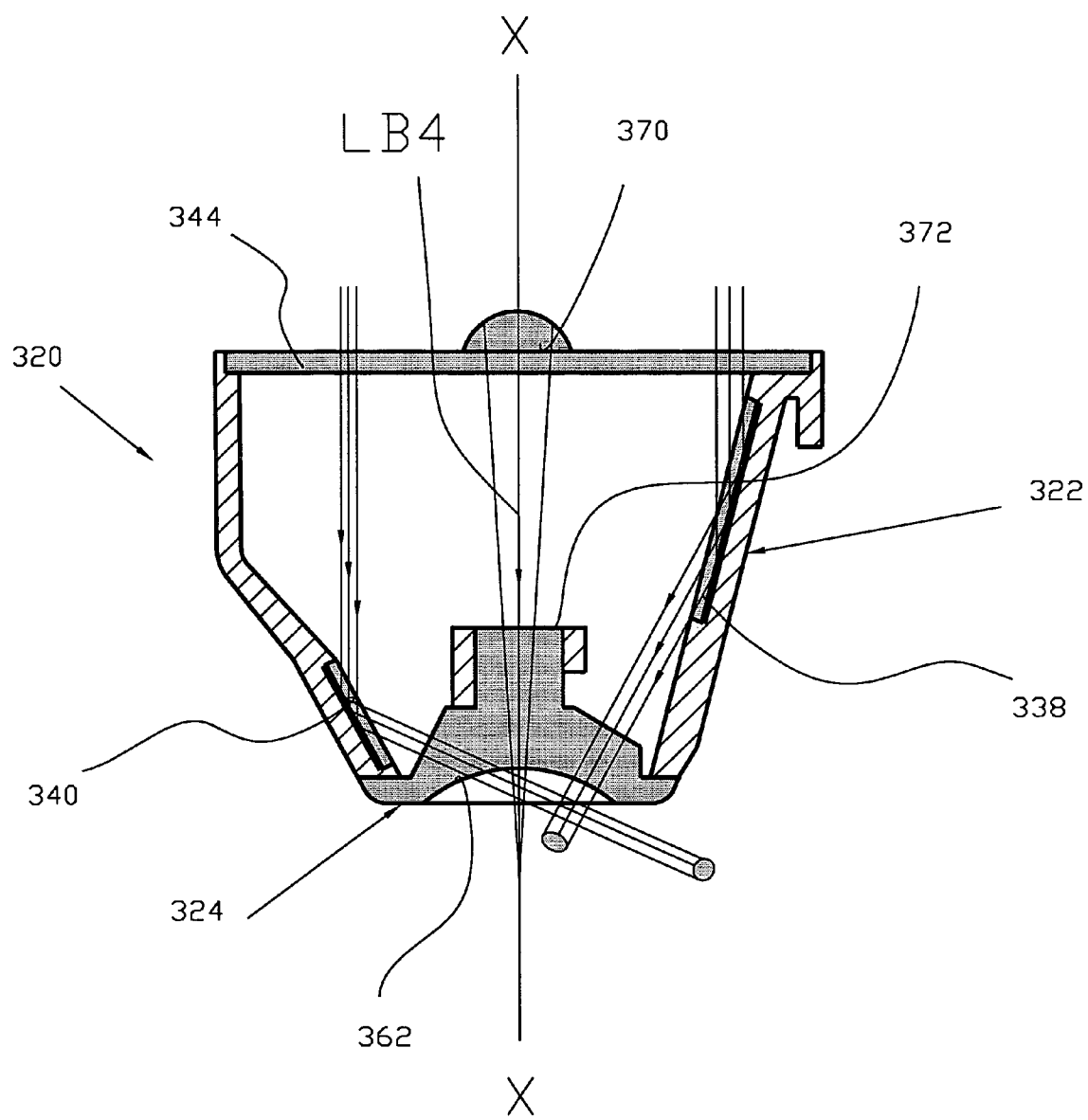
FIG. 7 is a longitudinal cross-sectional view of the universal gonioscope-lens system made in accordance with a further embodiment, wherein the laser-beam focusing lens is located on the gonioscope body cover.

The gonioscope-lens system 320 of the embodiments shown in FIG. 7 is practically the same as the one shown in FIG. 6, with the exception that the rear end face 372 of the contact lens 324 is flat, and the convex lens 370 for the laser beam LB4 is formed on the upper side of the transparent cover 344 located on the rear end of the gonioscope body 322.

Figure 8:
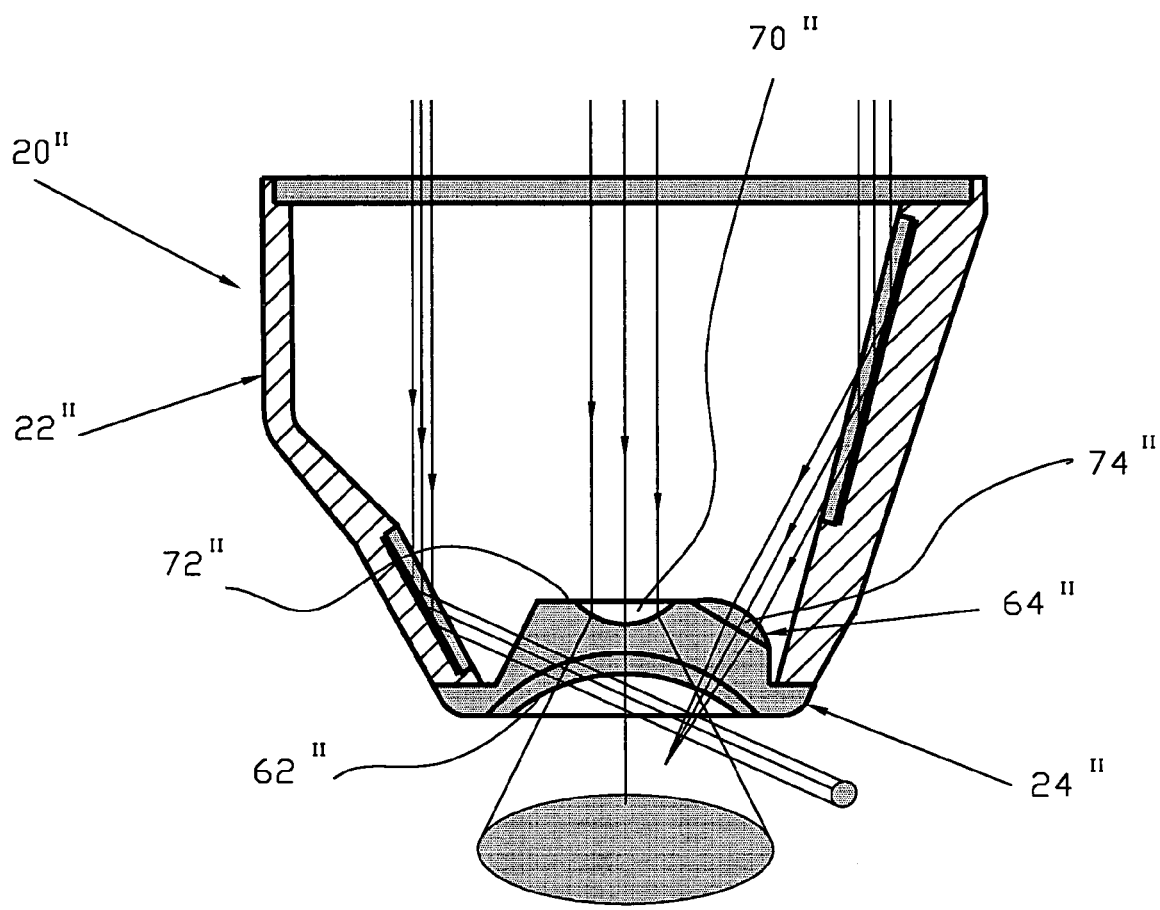
FIGS. 8 through 12 are the same views as shown in FIGS. 2, 4–7, respectively, for embodiments of the gonioscope/contact lens system having contact lenses with the prismatic main rear optical portion without the tail portion.

FIG. 8 is longitudinal sectional view of a gonioscope/contact lens system 20" similar to FIG. 2 with the exception that a contact lens 24" of this embodiment does not have a tail portion 64 and that the concave lens 70" is formed on the rear end face 72" of a rearwardly tapered portion 64" of the contact lens 24". The remaining parts of the contact lens that are the same as in the system of FIG. 2 are designated by the same reference numerals with an addition of two primes and their description is omitted. Thus the front concave surface is designated as 62", the convex lens is designated as 74", etc. The gonioscope/contact lens system 20" operates in the same manner as the one shown and described with reference to FIG. 2.

Figure 9:
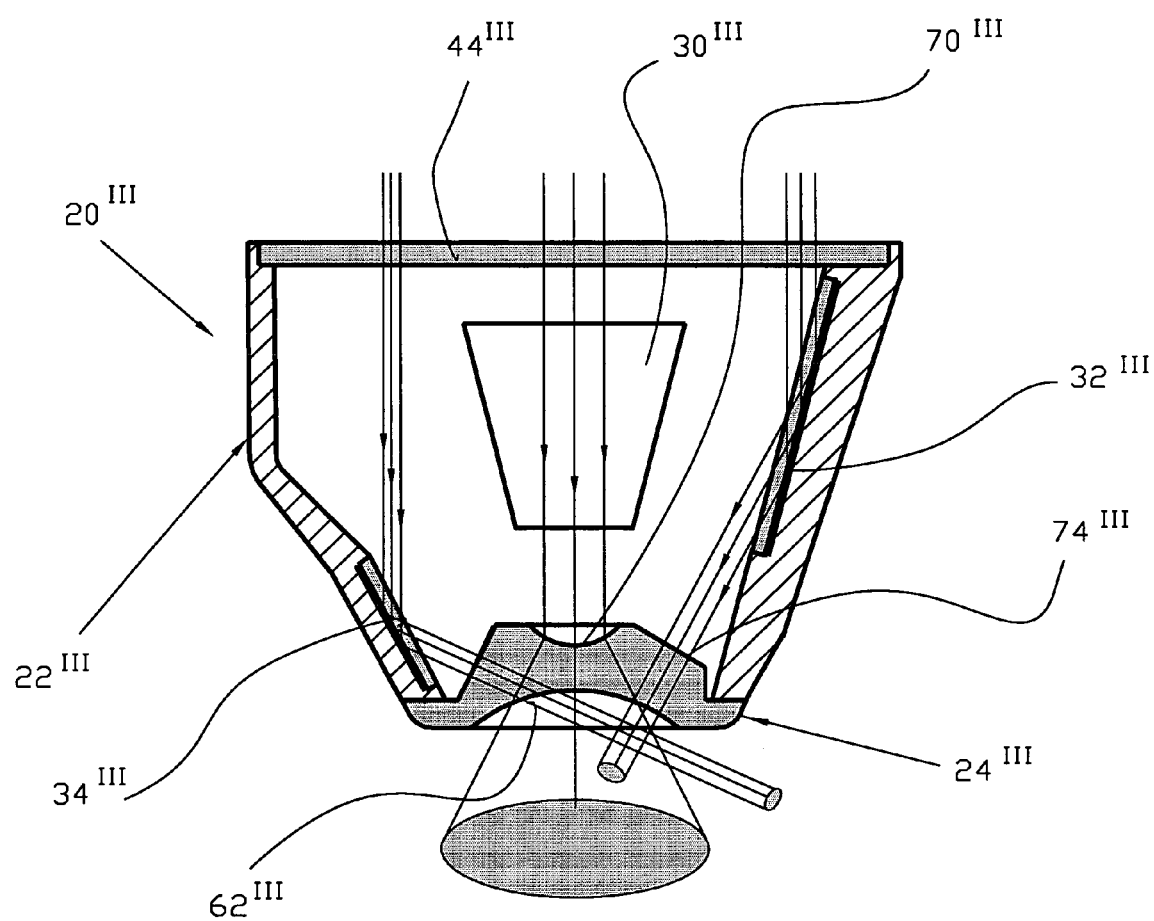

FIG. 9 is longitudinal sectional view of a gonioscope/contact lens system 20''' similar to FIG. 4 with the exception that a contact lens 24''' of this embodiment does not have a tail portion 64 and that the concave lens 70''' is formed on the rear end face 72' of a rearwardly tapered portion 64' of the contact lens 24'. The remaining parts of the contact lens 24' that are the same as in the system of FIG. 2 are designated by the same reference numerals with an addition of a three primes and their description is omitted. Thus the front concave surface is designated as 62''', the flat 74' is designated as 74''', etc. The gonioscope/contact lens system 20''' operates in the same manner as the one shown and described with reference to FIG. 4.

Figure 10:
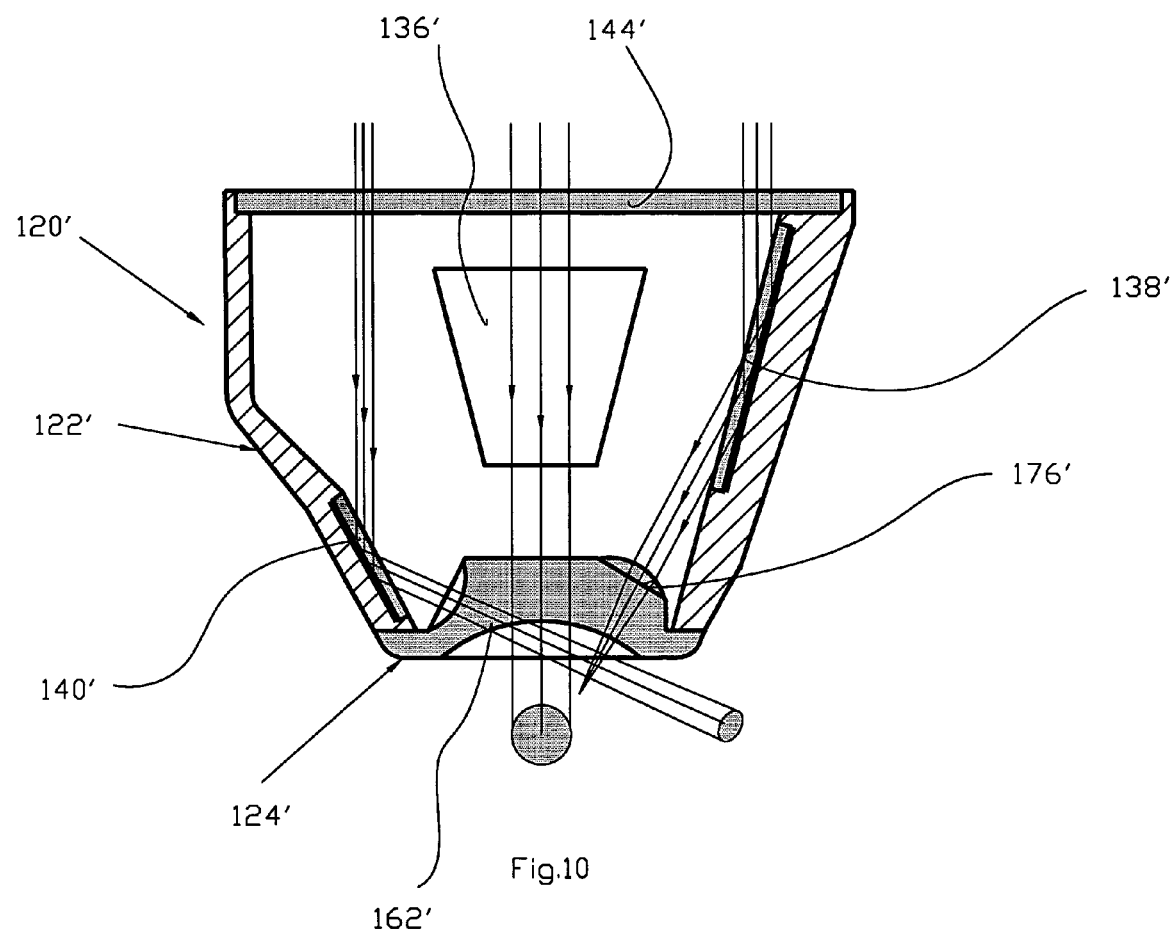

FIG. 10 is longitudinal sectional view of a gonioscope/contact lens system 120' similar to FIG. 5 with the exception that a contact lens 124' of this embodiment does not have a tail portion 164. The remaining parts of the contact lens that are the same as in the system of FIG. 5 are designated by the same reference numerals with an addition of a prime and their description is omitted. Thus the front concave surface is designated as 162', the convex lens is designated as 176', etc. The gonioscope/contact lens system 120' operates in the same manner as the one shown and described with reference to FIG. 5.

Figure 11:
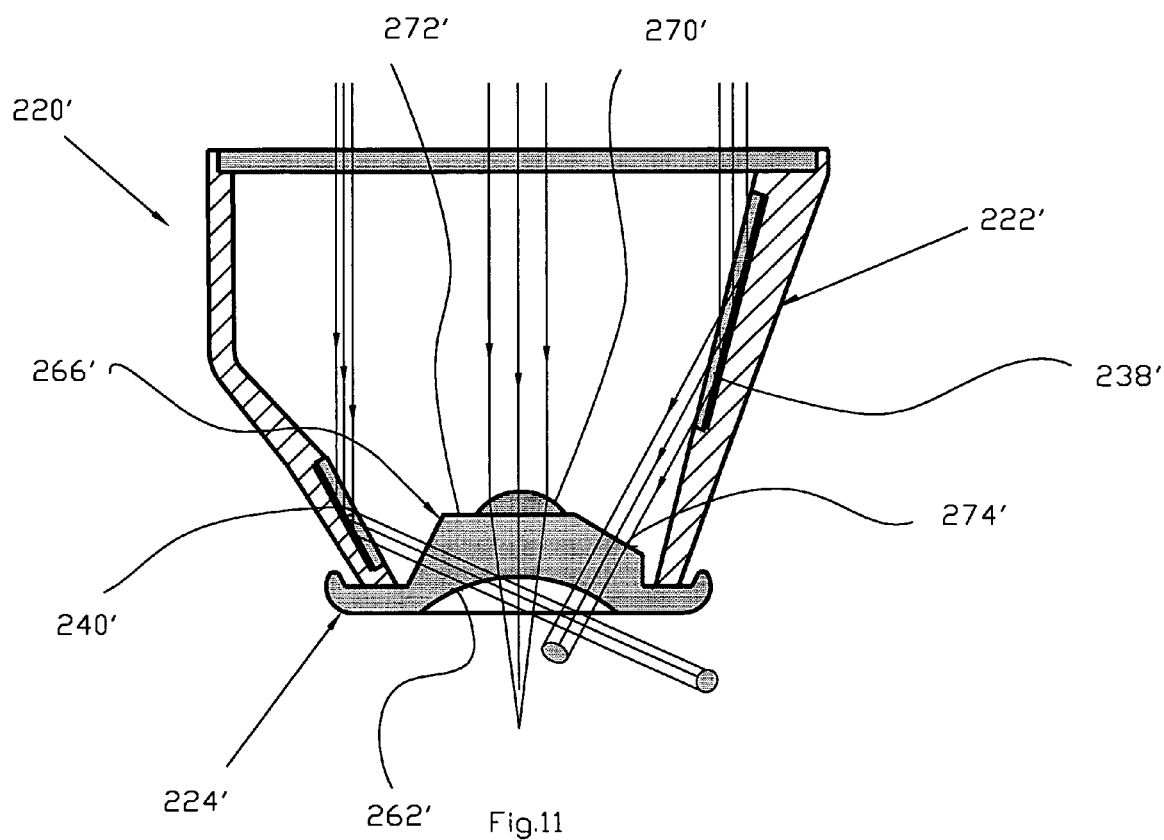

FIG. 11 is longitudinal sectional view of a gonioscope/contact lens system 220' similar to FIG. 6 with the exception that a contact lens 224' of this embodiment does not have a tail portion 64 and that the concave lens 270' is formed on the rear end face 272' of a rearwardly tapered portion 266' of the contact lens 224'. The remaining parts of the contact lens that are the same as in the system of FIG. 6 are designated by the same reference numerals with an addition of a prime and their description is omitted. Thus the front concave surface is designated as 262', the flat area is designated as 274', etc. The gonioscope/contact lens system 220' operates in the same manner as the one shown and described with reference to FIG. 6.

Figure 12:
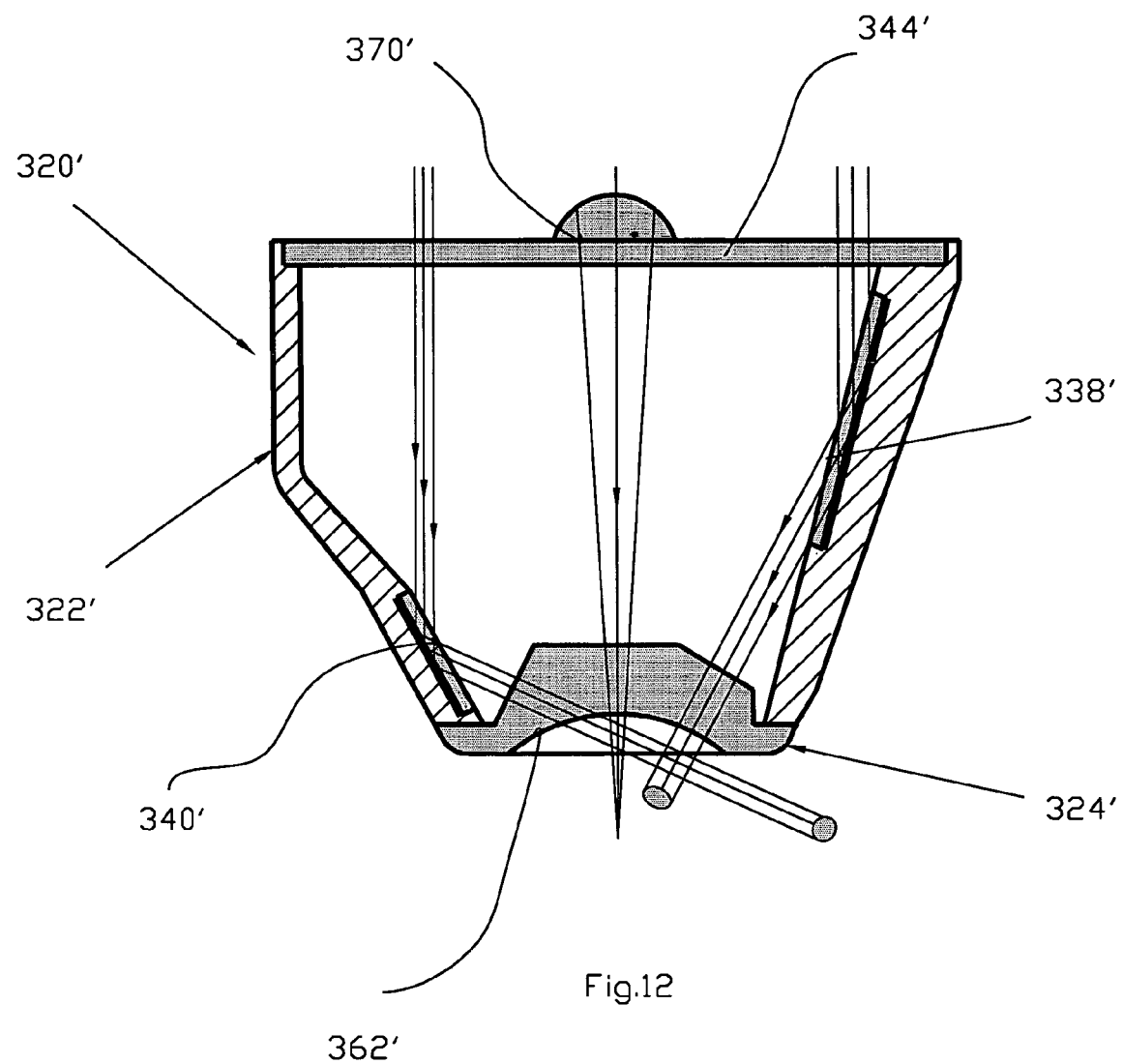

FIG. 12 is longitudinal sectional view of a gonioscope/contact lens system 320' similar to FIG. 7 with the exception that a contact lens 324' of this embodiment does not have a tail portion 364. The remaining parts of the contact lens that are the same as in the system of FIG. 7 are designated by the same reference numerals with an addition of a prime and their description is omitted. Thus the front concave surface is designated as 362', the convex lens 370 is designated as 370', etc. The gonioscope/contact lens system 320' operates in the same manner as the one shown and described with reference to FIG. 7.

Figure 13:
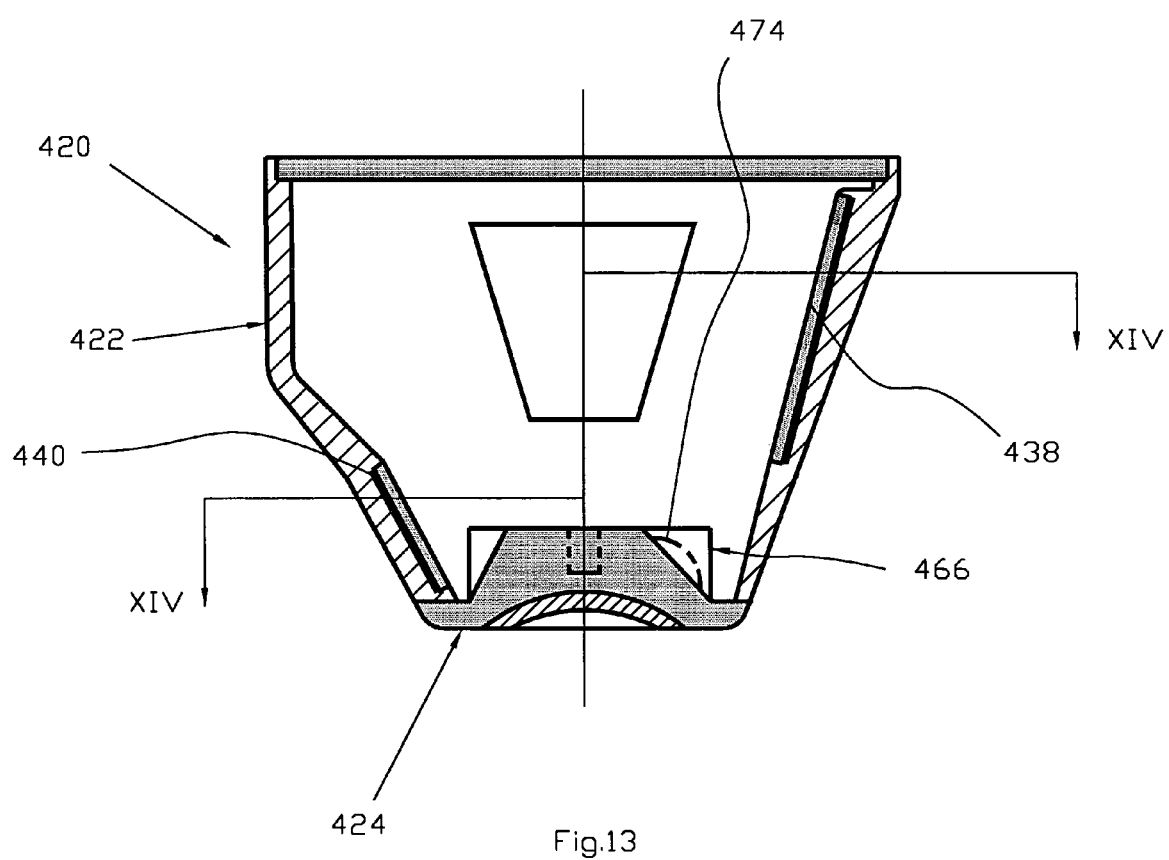
FIG. 13 is a view similar to FIG. 8 with a non-prismatic shape of the main rear optical portion.
Figure 14:
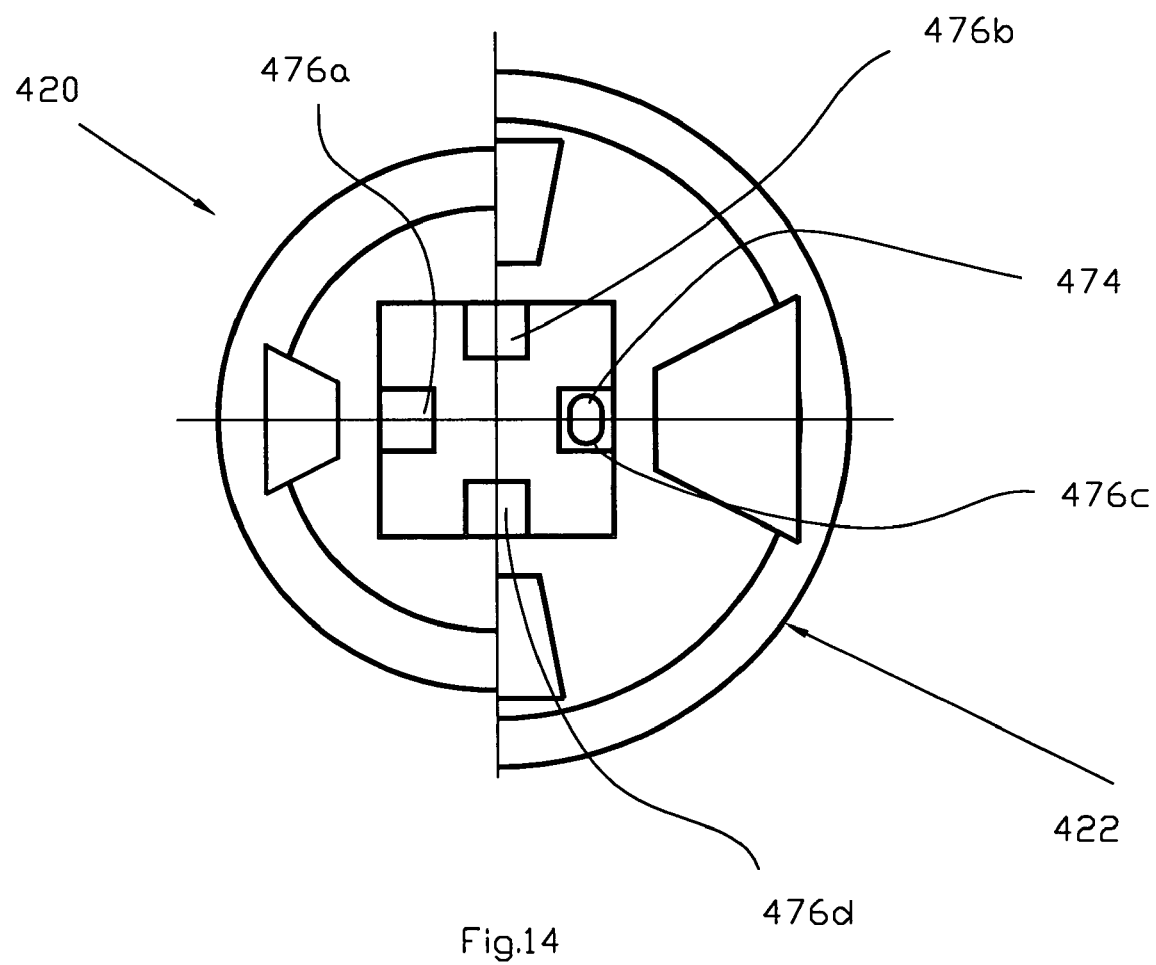
FIG. 14 is a top sectional view of the device of FIG. 13 along lines XIV—XIV.

FIG. 13 is a view of an embodiment of a gonioscope/lens system 420 similar, e.g., to the system of FIG. 8 but with a non-prismatic shape of the main rear optical portion. FIG. 14 is a top view of the device of FIG. 13. In fact, the main rear optical portion is not necessarily tapered or conical and may have any arbitrary configuration, provided that this optical portion has flat surfaces arranged perpendicular to the beams reflected from the reflecting mirrors of the gonioscopic body. Thus, as shown in FIGS. 13 and 14, the rear main optical portion 466 of a gonioscope/lens system 420 is made in the form of a cubical body with inclined surfaces or flats 476a, 476b, 476c, and 476d formed on the bottoms of the beveled recesses cut in the cubical body 464. A convex lens 474 of this system is formed on the beveled surface 476c. The rest of the system 420 is the same as in the embodiment of FIG. 8. It is understood that the cubical shape of the main rear optical portion was shown as modification of the embodiment of FIG. 8 only as an example and that this part of the contact lens may have a cubical or any other shape in application to the modified forms of the systems shown in FIGS. 9 through 12.

Figure 15:
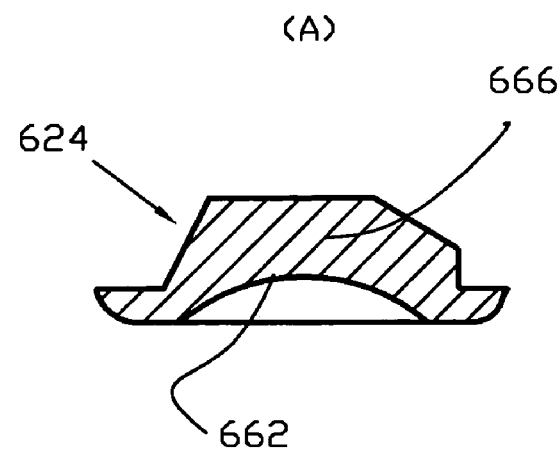
FIGS. 15 (A), (B), and (C) shows different structural modifications of monolithic and composite contact lenses.
Figure 15:
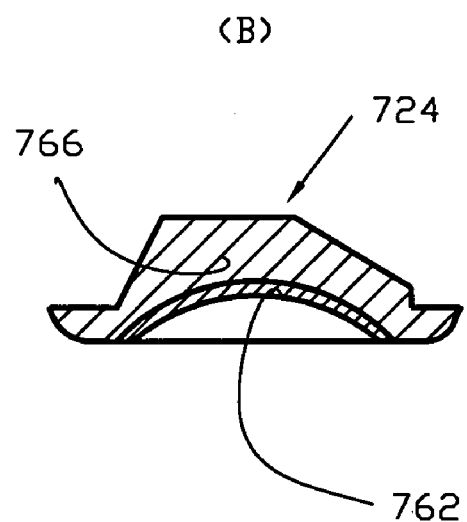
Figure 15:
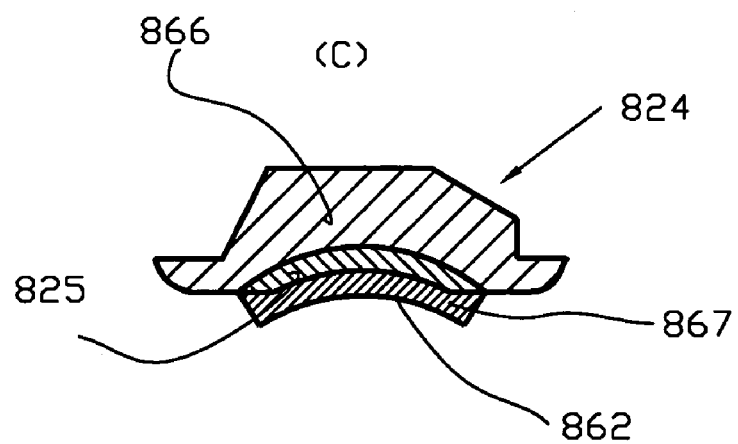

FIGS. 15(A), (B), and (C) shows different structural modifications of monolithic and composite contact lenses. In the modification of FIG. 15(A) the entire optical lens 624 with an appropriate front contact portion 662 and rear main optical portion 666 is made as a monolithic disposable body from a soft acrylic, silicone, or urethane plastic. In the modification of a contact lens 724 shown in FIG. 15(B), the rear main optical portion 766 is made from a rigid optical material such as optical glass while a portion with the front concave area 762 that is intended for contact with the cornea of the patient's eye is made from a soft temperature-resistant plastic insert that is permanently attached to the portion 766, e.g., via an optical glue or by polymerization. The entire unit may be intended for multiple use and can be sterilized. In the modification of a contact lens 824 shown in FIG. 15(C), the rear main optical portion 866 is made from a rigid optical material such as optical glass while a portion 867 with the front concave area 862 is replaceable and is made in the form of a thin optical segment shaped with a curvature matching the patient's cornea and removably attachable to the front end face of the rear main optical portion, e.g, via a biocompatible gel 825 and held on the aforementioned end face due to the forces of molecular attraction.

Thus, it has been shown that the present invention provides a gonioscope suitable for both intraocular laser surgery and diagnostic observation, which is equipped with a contact lens for supporting the gonioscope on the patient's eye and provides efficient delivery of laser and illumination beams through a simplified optical system. The contact lens of a laser/observation gonioscope has a design suitable for efficient delivery of both laser and illumination beam through the body of the lens. The gonioscope body can be cemented to the contact lens or the lens, or can be made separately for cooperation with a plurality of interchangeable gonioscope bodies. The contact lens can be used as a guiding support for sliding the body over the surface of the lens. The contact lens has a tail portion that facilitates handling of the lens, and the central part of the lens may be actively used for passing optical beams.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, such features as the convex lens on the back end face of the tail portion of the contact lens, arrangement of the lenses on the gonioscope cover, arrangement of the laser beam focusing lens and illumination light lens on the tapered portion, etc., can be used in combinations different from those described in the specification and shown in the specific drawings. The tail portion of the contact lens can be made as a separate part cemented to the lens head.

The invention claimed is:

1. A universal gonioscope-contact lens system suitable for observation and intraocular laser surgery comprising:
    a hollow gonioscope body having an optical axis and an inner surface with at least one light-reflecting means on said inner surface for reflecting a beam, which is incident on said at least one light-reflecting means in the direction parallel to said optical axis; and
    a contact lens portion for placing onto a patient's eye, said contact lens serving as a support for said hollow gonioscope body and comprising a front contact lens portion intended for contact with the patient's eye and a rear main optical portion of any arbitrary shape that has at least one flat surface;
    said at least one light-reflecting means on said inner surface being inclined at an acute angle to said optical axis so that when said incident beam parallel to said optical axis is reflected from said light-reflecting means, said incident beam will fall onto said at least one flat surface in a substantially perpendicular direction.

2. The universal gonioscope-contact lens system of claim 1, wherein said rear main optical portion has a rear end face, a side surface, and at least one optical lens component formed on said rear main optical portion.

3. The universal gonioscope-contact lens system of claim 2, wherein said at least one optical lens component is selected from the group consisting of a concave lens, and a convex lens.

4. The universal gonioscope-contact lens system of claim 3, wherein said at least one optical lens component is located on a part of said rear main optical portion selected from the group consisting of said rear end face and said side surface.

5. The universal gonioscope-contact lens system of claim 4, wherein said arbitrary shape is a shape tapered rearwardly from said contact lens portion and having a tapered surface, said at least one flat surface being formed on said tapered surface.

6. The universal gonioscope-contact lens system of claim 5, further comprising a tail portion extending rearwardly from said rear end face so that said tapered surface is located between said tail portion and said contact lens portion.

7. The universal gonioscope-contact lens system of claim 6, wherein said at least one optical lens component is located on a part of said rear main optical portion selected from the group consisting of said rear end face, said side surface, and said tail portion.

8. The universal gonioscope-contact lens system of claim 1, wherein said contact lens portion is selected from a group consisting of:
   a monolithic optical lens component made from a soft optical material;
   a composite optical lens component having on said front contact lens portion a permanently connected insert made from a material softer than said optical lens component that is intended for contact with a patient's eye; and
   a composite optical lens component having on said front contact lens portion a removable connected insert made from a material softer than said optical lens component that is intended for contact with a patient's eye.

9. The universal gonioscope-contact lens system of claim 8, wherein said monolithic optical lens is disposable and is made from a biocompatible soft plastic.

10. The universal gonioscope-contact lens system of claim 9, wherein said biocompatible soft plastic is selected from the group consisting of soft acrylic, silicone, and polyurethane.

11. The universal gonioscope-contact lens system of claim 4, wherein said contact lens portion is selected from a group consisting of:
   a monolithic optical lens component made from a soft optical material;
   a composite optical lens component having on said front contact lens portion a permanently connected insert made from a material softer than said optical lens component that is intended for contact with a patient's eye; and
   a composite optical lens component having on said front contact lens portion a removable connected insert made from a material softer than said optical lens component that is intended for contact with a patient's eye.

12. The universal gonioscope-contact lens system of claim 11, wherein said monolithic optical lens is disposable and is made from a biocompatible soft plastic.

13. The universal gonioscope-contact lens system of claim 12, wherein said biocompatible soft plastic is selected from the group consisting of soft acrylic, silicone, and polyurethane.

14. The universal gonioscope-contact lens system of claim 5, wherein said contact lens portion is selected from a group consisting of:
   a monolithic optical lens component made from a soft optical material;
   a composite optical lens component having on said front contact lens portion a permanently connected insert made from a material softer than said optical lens component that is intended for contact with a patient's eye; and
   a composite optical lens component having on said front contact lens portion a removable connected insert made from a material softer than said optical lens component that is intended for contact with a patient's eye.

15. The universal gonioscope-contact lens system of claim 14, wherein said monolithic optical lens is disposable and is made from a biocompatible soft plastic.

16. The universal gonioscope-contact lens system of claim 15, wherein said biocompatible soft plastic is selected from the group consisting of soft acrylic, silicone, and polyurethane.

17. The universal gonioscope-contact lens system of claim 6, wherein said contact lens portion is selected from a group consisting of:
   a monolithic optical lens component made from a soft optical material;
   a composite optical lens component having on said front contact lens portion a permanently connected insert made from a material softer than said optical lens component that is intended for contact with a patient's eye; and
   a composite optical lens component having on said front contact lens portion a removable connected insert made from a material softer than said optical lens component that is intended for contact with a patient's eye.

18. The universal gonioscope-contact lens system of claim 17, wherein said monolithic optical lens is disposable and is made from a biocompatible soft plastic.

19. The universal gonioscope-contact lens system of claim 18, wherein said biocompatible soft plastic is selected from the group consisting of soft acrylic, silicone, and polyurethane.

20. The universal gonioscope-contact lens system of claim 1, wherein said contact lens has an engagement with said hollow gonioscope body selected from the groups consisting of a rigid-connection engagement with said gonioscope body, an engagement that allows for free disconnection from said gonioscope body by movement in the direction of said optical axis but without possibility of movement in the direction transverse to said optical axis; and an engagement that allows for free disconnection of said gonioscope body from said contact lens by movement in the direction of said optical axis and possibility of movement in the direction transverse to said optical axis.

21. The universal gonioscope-contact lens system of claim 4, wherein said contact lens has an engagement with said hollow gonioscope body selected from the groups consisting of a rigid-connection engagement with said gonioscope body, an engagement that allows for free disconnection from said gonioscope body by movement in the direction of said optical axis but without possibility of movement in the direction transverse to said optical axis; and an engagement that allows for free disconnection of said gonioscope body from said contact lens by movement in the direction of said optical axis and possibility of movement in the direction transverse to said optical axis.

22. The universal gonioscope-contact lens system of claim 21, wherein said contact lens portion is selected from a group consisting of:
   a monolithic optical lens component made from a soft optical material;
   a composite optical lens component having on said front contact lens portion a permanently connected insert made from a material softer than said optical lens component that is intended for contact with a patient's eye; and
   a composite optical lens component having on said front contact lens portion a removable connected insert made from a material softer than said optical lens component that is intended for contact with a patient's eye.

23. The universal gonioscope-contact lens system of claim 22, wherein said monolithic optical lens is disposable and is made from a soft biocompatible soft plastic.

* * * * *